United States Patent
Matsuki et al.

(10) Patent No.: US 9,825,239 B2
(45) Date of Patent: Nov. 21, 2017

(54) BENZINDOLOCARBAZOLE DERIVATIVE, LIGHT-EMITTING ELEMENT MATERIAL PRODUCED USING SAME, AND LIGHT-EMITTING ELEMENT

(71) Applicant: TORAY Industries, Inc., Tokyo (JP)

(72) Inventors: Shinichi Matsuki, Otsu (JP); Daisaku Tanaka, Otsu (JP); Takeshi Ikeda, Otsu (JP); Atsushi Ikeda, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 298 days.

(21) Appl. No.: 14/436,174

(22) PCT Filed: Oct. 10, 2013

(86) PCT No.: PCT/JP2013/077589
§ 371 (c)(1),
(2) Date: Apr. 16, 2015

(87) PCT Pub. No.: WO2014/061546
PCT Pub. Date: Apr. 24, 2014

(65) Prior Publication Data
US 2015/0280140 A1    Oct. 1, 2015

(30) Foreign Application Priority Data

Oct. 18, 2012 (JP) ................ 2012-230464

(51) Int. Cl.
| | |
|---|---|
| *H01L 51/00* | (2006.01) |
| *C07D 487/04* | (2006.01) |
| *C09K 11/06* | (2006.01) |
| *H05B 33/14* | (2006.01) |
| *H01L 51/50* | (2006.01) |
| *H01L 51/52* | (2006.01) |

(52) U.S. Cl.
CPC ........ *H01L 51/0072* (2013.01); *C07D 487/04* (2013.01); *C09K 11/06* (2013.01); *H01L 51/006* (2013.01); *H01L 51/0052* (2013.01); *H01L 51/0061* (2013.01); *H01L 51/0067* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1048* (2013.01); *C09K 2211/1051* (2013.01); *C09K 2211/1059* (2013.01); *C09K 2211/1074* (2013.01); *H01L 51/5016* (2013.01); *H01L 51/5024* (2013.01); *H01L 51/5056* (2013.01); *H01L 51/5088* (2013.01); *H01L 51/5206* (2013.01); *H01L 51/5221* (2013.01); *H01L 51/5231* (2013.01)

(58) Field of Classification Search
None
See application file for complete search history.

(56) References Cited

U.S. PATENT DOCUMENTS

| | | | | |
|---|---|---|---|---|
| 5,843,607 A | * | 12/1998 | Hu | ........ G03G 5/0653 430/58.5 |
| 2009/0302742 A1 | | 12/2009 | Komori et al. | |
| 2011/0062429 A1 | * | 3/2011 | Kai | ........ C07D 487/04 257/40 |
| 2012/0001165 A1 | * | 1/2012 | Komori | ........ C07D 403/14 257/40 |
| 2012/0007070 A1 | | 1/2012 | Kai et al. | |

FOREIGN PATENT DOCUMENTS

| | | |
|---|---|---|
| WO | WO 2007/063754 A1 | 6/2007 |
| WO | WO 2010/113761 A1 | 10/2010 |
| WO | WO 2011/136483 A1 | 11/2011 |
| WO | WO 2013/154325 A1 | 10/2013 |

OTHER PUBLICATIONS

International Search Report issued in PCT/JP2013/077589, dated Nov. 26, 2013.

* cited by examiner

*Primary Examiner* — Robert S Loewe
(74) *Attorney, Agent, or Firm* — Birch, Stewart, Kolasch & Birch, LLP

(57) ABSTRACT

The present invention provides an organic thin film light emitting device having high luminous efficiency and durable life realized by using a benzindolocarbazole derivative as represented by either general formula (1-1) or (1-2) given below:
[Chemical compound 1]
wherein $R^1$ to $R^{24}$ may be identical to or different from each other and are selected from the group consisting of a hydrogen atom, alkyl group, cycloalkyl group, heterocyclic group, amino group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group, carbamoyl group, silyl group, and —$P(=O)R^{25}R^{26}$; $R^{25}$ and $R^{26}$ represent either an aryl group or a heteroaryl group; $R^{25}$ and $R^{26}$ may be condensed to form a ring; $L^1$ to $L^4$ independently represent a single bond, a substituted or unsubstituted arylene group, or a substituted or unsubstituted heteroarylene group; and $A^1$ to $A^4$ independently represent an amino group, aryl group, heterocyclic group, or heteroaryl group.

20 Claims, No Drawings

BENZINDOLOCARBAZOLE DERIVATIVE, LIGHT-EMITTING ELEMENT MATERIAL PRODUCED USING SAME, AND LIGHT-EMITTING ELEMENT

TECHNICAL FIELD

The present invention relates to a benzindolocarbazole derivative that is used suitably in light emitting devices that can convert electric energy to light and organic-field devices such as organic thin film solar batteries. More specifically, the invention relates to light emitting devices and organic field devices that can be used in such fields as display devices, flat panel displays, backlights, lighting equipment, interior decoration devices, indicators, advertising displays, electrophotographic devices, and optical signal generating devices, and also relates a benzindolocarbazole derivative that is used therein.

BACKGROUND ART

Active studies have been performed in recent years for the development of organic thin film light emitting devices that contain electrodes and an organic fluorescent substance located between them in which electrons injected from the cathode and holes injected from the anode are recombined to emit light. These light emitting devices have attracted attention particularly because of their features such as a thin body, high luminance light emission under a low driving voltage, and multi-color light emission realized by specific type of fluorescent materials.

Since C. W. Tang et. al at Kodak found that an organic thin film device emits light with high luminance, various studies have been carried out to provide practical devices, resulting in the application of organic thin film devices to a variety of instruments such as main displays of portable telephones. However, there still remain many technical problems and one of the major issues is to provide a device that realizes both a high efficiency and a long life.

The required driving voltage for a device depends largely on the carrier transport material used to transport carriers, i.e. holes and electrons, to the light emitting layer. Of these, known materials that can transport holes (hole transport materials) include substances containing an amine backbone (see, for example, Patent documents 1 to 2), a carbazole backbone (see, for example, Patent document 3), or an indolocarbazole backbone (see, for example, Patent document 4). Substances containing an amine backbone are useful because they show high hole transport performance, but they suffers a significant deterioration in triplet energy as a result of an excessively long conjugation. Therefore, they cannot work effectively in confining triplet excitons particularly from a phosphorescene emitting layer, resulting in a low luminous efficiency. In addition, there also remain problems concerning the heat resistance of materials and durability of devices. Furthermore, it is known that substances containing a carbazole backbone or indolocarbazole backbone are high in the triplet level and it has been proposed to use them as material for phosphorescene emitting layers or material for confining triplet excitons from a phosphorescene emitting layer (see, for example, Patent document 5). Accordingly, they are particularly suitable for devices that require high triplet energy, such as green phosphorescent devices. However, substances high in triplet energy generally tend to be high in singlet energy and inevitably high in ionization potential. Therefore, devices that do not require a very large triplet energy, such as fluorescent devices and red phosphorescent devices, will need an increased driving voltage, leading to a decrease in luminous efficiency and a deterioration in device durability.

PRIOR ART DOCUMENTS

Patent Documents

Patent document 1: Japanese Patent No. 3828595
Patent document 2: Japanese Patent No. 3194657
Patent document 3: Japanese Patent No. 3139321
Patent document 4: International Publication 2007/063754
Patent document 5: International Publication WO2010/113761

SUMMARY OF THE INVENTION

Problems to be Solved by the Invention

As described above, it is difficult for the conventional techniques to decrease the driving voltage sufficiently and even if the driving voltage can be decreased, it will be impossible to provide a device that has both a high luminous efficiency and a long durable life. Thus, no efforts have been successful in providing a technique that can achieve both a high luminous efficiency and a long durable life.

An object of the present invention is to solve these problems with the conventional techniques and provide an organic thin film light emitting device having an improved luminous efficiency and durable life.

Means of Solving the Problems

The present invention provides a benzindolocarbazole derivative as represented by general formula (1-1) or (1-2) given below.

[Chemical formula 1]

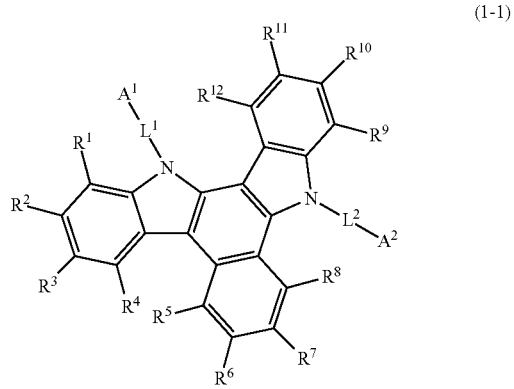

(1-1)

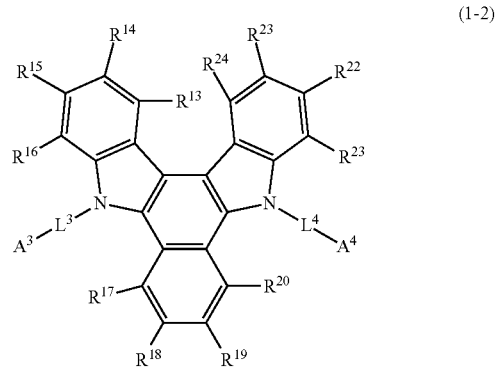

(1-2)

In the formula, $R^1$ to $R^{24}$ may be identical to or different from each other and are selected from the group consisting of a hydrogen atom, alkyl group, cycloalkyl group, heterocyclic group, amino group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group, carbamoyl group, silyl group, and —P(=O)$R^{25}R^{26}$. $R^{25}$ and $R^{26}$ represent either an aryl group or a heteroaryl group. $R^{25}$ and $R^{26}$ may be condensed to form a ring. $L^1$ to $L^4$ independently represent a single bond, a substituted or unsubstituted arylene group, or a substituted or unsubstituted heteroarylene group. $A^1$ to $A^4$ independently represent an amino group, aryl group, heterocyclic group, or heteroaryl group.

Advantageous Effect of the Invention

The present invention can provide an organic electric field light emitting device that is low in driving voltage, high in luminous efficiency, and sufficiently long in durable life.

DESCRIPTION OF PREFERRED EMBODIMENTS

Described in detail below are benzindolocarbazole derivatives according to the present invention that are represented by general formula (1-1) or (1-2).

[Chemical formula 2]

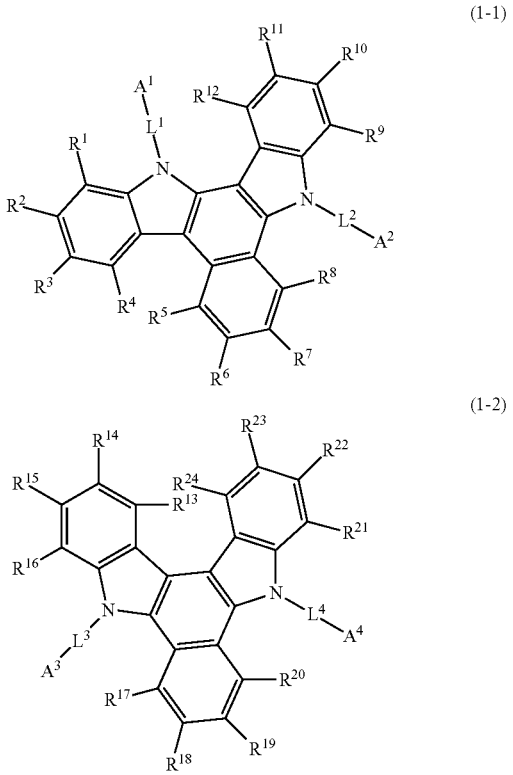

In the formula, $R^1$ to $R^{24}$ may be identical to or different from each other and are selected from the group consisting of a hydrogen atom, alkyl group, cycloalkyl group, heterocyclic group, amino group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group, carbamoyl group, silyl group, and —P(=O)$R^{25}R^{26}$. $R^{25}$ and $R^{26}$ represent either an aryl group or a heteroaryl group. $R^{25}$ and $R^{26}$ may be condensed to form a ring. $L^1$ to $L^4$ independently represent a single bond, a substituted or unsubstituted arylene group, or a substituted or unsubstituted heteroarylene group. $A^1$ to $A^4$ independently represent an amino group, aryl group, heterocyclic group, or heteroaryl group.

In these substituent groups, the hydrogen atoms may be deuterium atoms. An alkyl group is a saturated aliphatic hydrocarbon group such as, for example, methyl group, ethyl group, n-propyl group, isopropyl group, n-butyl group, sec-butyl group, and tert-butyl group, which may or may not contain a substituent group. There are no specific limitations on the number of carbon atoms contained in an alkyl group, but commonly, from the viewpoint of availability and cost, it is preferably in the range of 1 or more and 20 or less, more preferably 1 or more and 8 or less.

A cycloalkyl group is a saturated alicyclic hydrocarbon group such as, for example, cyclopropyl, cyclohexyl, norbornyl, and adamantyl, which may or may not contain a substituent group. There are no specific limitations on the number of carbon atoms in an alkyl group portion, but commonly it is in the range of 3 or more and 20 or less.

A heterocyclic group has either an aliphatic ring containing an atom other than carbon such as, for example, pyran ring, piperidine ring, and cyclic amide, or a combination of two aromatic rings connected via a carbon atom or a heteroatom such as phenoxazine ring, dibenzothiazine ring, and dihydroacridine ring, which may or may not contain a substituent group. There are no specific limitations on the number of carbon atoms in a heterocyclic group, but commonly it is in the range of 2 or more and 20 or less.

An amino group may or may not contain a substituent group and useful substituent groups include, for example, alkyl group, aryl group, and heteroaryl group. These substituent groups may be further substituted.

An alkenyl group is an unsaturated aliphatic hydrocarbon group containing a double bond such as, for example, vinyl group, allyl group, and butadienyl group, which may or may not contain a substituent group. There are no specific limitations on the number of carbon atoms in an alkenyl group, but commonly it is in the range of 2 or more and 20 or less.

A cycloalkenyl group is an unsaturated alicyclic hydrocarbon group containing a double bond such as, for example, cyclopentenyl group, cyclopentadienyl group, and cyclohexenyl group, which may or may not contain a substituent group. There are no specific limitations on the number of carbon atoms in a cycloalkenyl group, but commonly it is in the range of 2 or more and 20 or less.

An alkynyl group is an unsaturated aliphatic hydrocarbon group containing a triple bond such as, for example, ethynyl group, which may or may not contain a substituent group. There are no specific limitations on the number of carbon atoms in an alkynyl group, but commonly it is in the range of 2 or more and 20 or less.

An alkoxy group is a functional group composed of an aliphatic hydrocarbon group and an ether bond bonded thereto such as, for example, methoxy group, ethoxy group, and propoxy group, and the aliphatic hydrocarbon group may or may not contain a substituent group. There are no specific limitations on the number of carbon atoms in an alkoxy group, but preferably it is in the range of 1 or more and 20 or less.

An alkylthio group has the same structure as the corresponding alkoxy group except that the oxygen atom in the ether bond is replaced with a sulfur atom. The hydrocarbon group contained in an alkylthio group may or may not contain a substituent group. There are no specific limitations on the number of carbon atoms in an alkylthio group, but preferably it is in the range of 1 or more and 20 or less.

An aryl ether group is a functional group in which an aromatic hydrocarbon group is bonded through an ether bond such as, for example, phenoxy group, and the aromatic hydrocarbon group may or may not contain a substituent group. There are no specific limitations on the number of carbon atoms in an aryl ether group, but preferably it is in the range of 6 or more and 40 or less.

An aryl thioether group has the same structure as the corresponding aryl ether group except that the oxygen atom in the ether bond is replaced with a sulfur atom. The aromatic hydrocarbon group contained in an aryl ether group may or may not contain a substituent group. There are no specific limitations on the number of carbon atoms in an aryl ether group, but preferably it is in the range of 6 or more and 40 or less.

An aryl group is an aromatic hydrocarbon group such as, for example, phenyl group, biphenyl group, fluorenyl group, phenanthryl group, triphenylenyl group, and terphenyl group. An aryl group may or may not contain a substituent group. There are no specific limitations on the number of carbon atoms in an aryl group, but commonly it is in the range of 6 or more and 40 or less.

A heteroaryl group is a cyclic aromatic group containing one or more atoms other than carbon such as furanyl group, thiophenyl group, pyridyl group, pyrazinyl group, pyrimidinyl group, triazinyl group, benzofuranyl group, benzothiophenyl group, and indolyl group, which may be unsubstituted or substituted. There are no specific limitations on the number of carbon atoms in a heteroaryl group, but commonly it is in the range of 2 or more and 30 or less.

It is a cyclic aromatic group containing one or more atoms other than carbon such as furanyl group, thiophenyl group, pyridyl group, quinolinyl group, isoquinolinyl group, pyrazinyl group, pyrimidyl group, naphthyridyl group, benzofuranyl group, benzothiophenyl group, indolyl group, dibenzofuranyl group, dibenzothiophenyl group, and carbazolyl group, which may be unsubstituted or substituted. There are no specific limitations on the number of carbon atoms in a heteroaryl group, but preferably it is in the range of 2 or more and 30 or less.

A halogen atom is an atom selected from fluorine, chlorine, bromine, and iodine.

The carbonyl group, carboxyl group, oxycarbonyl group, carbamoyl group, and phosphine oxide group may or may not contain a substituent group. Here, the substituent group may be, for example, an alkyl group, cycloalkyl group, aryl group, or heteroaryl group, and these substituent groups may be further substituted.

A silyl group is a functional group containing a bond to a silicon atom such as, for example, trimethyl silyl group, which may or may not contain a substituent group. There are no specific limitations on the number of carbon atoms in a silyl group, but commonly it is in the range of 3 or more and 20 or less. The number of silicon atoms is commonly in the range of 1 or more and 6 or less.

An arylene group is a divalent group derived from an aryl group such as, for example, phenylene group, naphthylene group, biphenylene group, fluorenylene group, phenanthrylene group, terphenylene group, anthracenylene group, and pyrenylene group. These may or may not contain a substituent group. There are no specific limitations on the number of carbon atoms in an arylene group, but commonly it is in the range of 6 or more and 40 or less. For an arylene group containing a substituent group, the total number of carbon atoms including those in the substituent group is preferably in the range of 6 or more and 60 or less.

A heteroarylene group is a divalent or trivalent group derived from an aromatic group with a ring containing one or more atoms other than carbon such as pyridyl group, quinolinyl group, pyrimidinyl group, pyrazinyl group, naphthyridyl group, dibenzofuranyl group, dibenzothiophenyl group, and carbazolyl group, which may or may not contain a substituent group. There are no specific limitations on the number of carbon atoms in a heteroarylene group, but preferably it is in the range of 2 or more and 30 or less.

The compounds with a conventional amine backbone, carbazole backbone, or indolocarbazole that have been used conventionally as material for light emitting devices do not have sufficiently high performance. For example, N4,N4'-di(naphthalen-1-yl)-N4,N4'-diphenyl-[1,1'-biphenyl]-4,4'-diamine (abbreviated as NPD) has generally been used as material with an amine backbone. NPD is low in ionization potential and accordingly high in hole injection efficiency and has substituted naphthalene groups on nitrogen atoms that bring about a long conjugation and a high hole transport efficiency, but it has the problem of a low triplet energy, leading to a low luminous efficiency. There are other problems including a low glass transition temperature, which may influence the durability of devices. The structure of NPD is as shown below.

[Chemical formula 3]

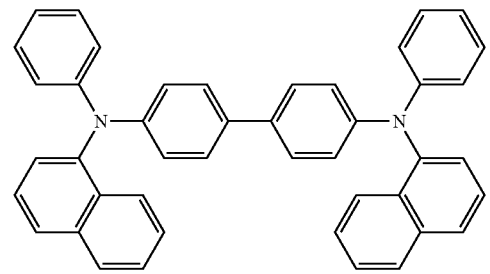

The compounds with carbazole backbone that have been used conventionally as material for light emitting devices do not necessarily have sufficiently high performance. For example, 9,9'-diphenyl-9H,9'H-3,3'-bicarbazole and 1,3-di(9H-carbazol-9-yl)benzene (abbreviated as mCP) is high in the triplet level and serves as general-purpose exciton blocking material. However, it is low in hole injection efficiency due to a high ionization potential and also low in hole transport efficiency due to a small conjugation length, leading to the problem of an increased driving voltage. The structures of 9,9'-diphenyl-9H,9'H-3,3'-bicarbazole and mCP are shown below.

[Chemical formula 4]

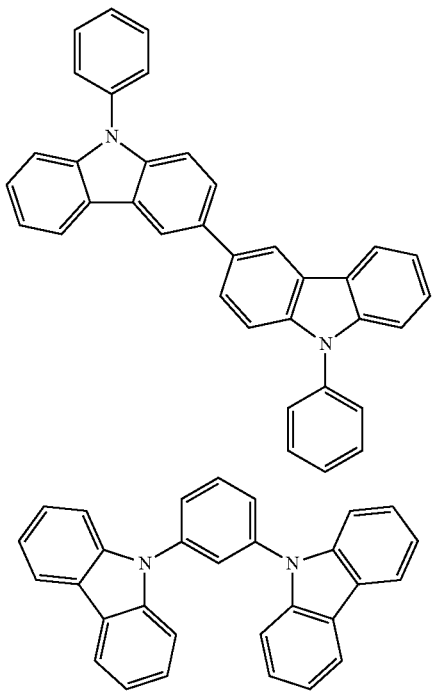

The compounds with an indolocarbazole backbone proposed in Patent document 4 are higher in hole transport efficiency than the conventional ones with a carbazole backbone, but high in ionization potential and low in hole injection efficiency, leading to the problem of an increased driving voltage. A typical compound proposed in Patent document 4 is shown below.

[Chemical formula 5]

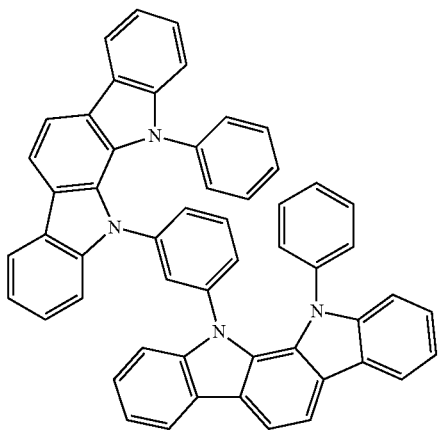

The inventors thought that because the compounds with an indolocarbazole backbone are generally poor in hole injection and transport characteristics, the proportion of the holes entering the light emitting layer is lower than that of the electrons coming from the electron transport layer and accordingly, the balance of electric charges in the light emitting layer breaks down, resulting in deterioration in the performance of the device.

Then, the inventors found that the existence of the benzindolocarbazole backbone, which is derived from the indolocarbazole backbone by replacing the central portion of the backbone with naphthalene, works to improve the hole transport efficiency and hole injection efficiency due to an increased conjugation length and a decreased ionization potential. Unlike the conventional amine-based backbones, the benzindolocarbazole backbone has a ring-fused structure and the movements of molecules are small even in an excited state, making it possible to maintain a higher triplet energy compared to the conventional amine-based hole transport materials including NPD. In addition, the steric hindrance of the naphthalene structure in a molecule allows the substituted group on a nitrogen atom to stand nearly perpendicular to the benzindolocarbazole backbone. Accordingly, the glass transition temperature rises to improve the stability of the thin film.

The benzindolocarbazole derivatives represented by general formula (1-1) or (1-2) tend to have a highly planar benzindolocarbazole backbone and therefore, their molecules can be stacked favorably, leading to a high hole transport efficiency. Furthermore, the electronic influence differs among the positions of the nitrogen atoms in a benzindolocarbazole backbone and they act effectively in decreasing the ionization potential when they are located at the para-positions of the central benzene ring. Therefore, the molecules represented by formula (1-2) are preferred from the viewpoint of increasing the hole injection efficiency. However, the molecules represented by formula (1-1) are preferred in terms of their synthesis because they can be synthesized more easily.

In the benzindolocarbazole derivatives represented by general formula (1-1) or (1-2), $L^1$ to $L^4$ independently denote a single bond, substituted or unsubstituted arylene group, or substituted or unsubstituted heteroarylene group, of which an unsubstituted arylene group or heteroarylene group is preferable from the viewpoint of preventing an excessive increase in conjugation length. Furthermore, an arylene group that is smaller in electronic influence is more preferable and the phenylene group, which has a moderate molecular weight, is the most preferable.

$A^1$ to $A^4$ independently denote an amino group, aryl group, heterocyclic group, or heteroaryl group and it is preferable that at least one of them is a group selected from those represented by any of general formulae (2) to (7).

[Chemical formula 6]

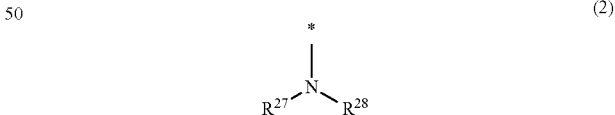

(2)

In the formulae, $R^{27}$ and $R^{28}$ may be identical to or different from each other and are selected from the group consisting of aryl group, heteroaryl group, polycyclic aromatic hydrocarbon group, and polycyclic aromatic heterocyclic group. It is connected to either $L^1$ or $L^2$ in general formula (1-1) given above or either $L^3$ or $L^4$ in general formula (1-2) given above at the position indicated by *.

If an amine backbone is contained as in general formula (2), the ionization potential of the benzindolocarbazole derivatives represented by general formula (1-1) or (1-2) decreases due to the electron-donating capacity of the amino group, leading to an improved hole injection efficiency.

It is most preferable for each of $R^{27}$ and $R^{28}$ to be an aryl group because of its moderate molecular weight, small electronic influence, and ability to increase the conjugation length, and in particular, it is preferably a phenyl group, biphenyl group, or dimethyl fluorenyl group from the viewpoint of maintaining a high triplet energy as well. These substituent groups may further contain a substituent group, and if containing a substituent group, it is preferably an alkyl group, particularly preferably a methyl group, because it does not influence on the conjugation length. Connection to either $L^1$ or $L^2$ in general formula (1-1) given above or either $L^3$ or $L^4$ in general formula (1-2) given above at the position indicated by * means that the nitrogen atom in general formula (2) is connected directly to either $L^1$ or $L^2$ in general formula (1-1) or either $L^3$ or $L^4$ in general formula (1-2).

Each of $L^1$ and $L^2$ in general formula (1-1) and $L^3$ and $L^4$ in general formula (1-2) is preferably an arylene group from the viewpoint of synthesis and in particular, it is preferably a phenylene group or a biphenylene group from the viewpoint of molecular weight. If a structure as represented by general formula (2) is connected to these groups, it is preferable for the nitrogen atom in general formula (2) to be connected to the para-position in the case of a phenylene group or to such a position as to form a 4-(4-aminophenyl) phenyl backbone in the case of a biphenylene group because the ionization potential will be small. Furthermore, from the viewpoint of synthesis, it is connected more preferably to $L^1$ in general formula (1-1) or $L^3$ in general formula (1-2).

[Chemical formula 7]

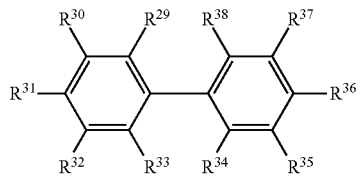

(3)

In the formula, $R^{29}$ to $R^{38}$ may be identical to or different from each other and are selected from the group consisting of a hydrogen atom, alkyl group, cycloalkyl group, aryl group, heterocyclic group, alkenyl group, cycloalkenyl group, alkynyl group, halogen atom, carbonyl group, carboxyl group, oxycarbonyl group, carbamoyl group, silyl group, and $—P(=O)R^{39}R^{40}$. $R^{39}$ and $R^{40}$ represent either an aryl group or a heteroaryl group. $R^{39}$ and $R^{40}$ may be condensed to form a ring. It is connected to either $L^1$ or $L^2$ in general formula (1-1) given above or either $L^3$ or $L^4$ in general formula (1-2) given above at the position of any of $R^{29}$ to $R^{38}$.

If a p-biphenyl backbone is contained as in general formula (3), the conjugation length is longer than in the case of a phenyl group, allowing the benzindolocarbazole derivatives represented by general formula (1-1) or (1-2) to have an improved carrier transport efficiency. It is also preferable because they have a moderate molecular weight and the compounds have an increased glass transition temperature, leading to a thin film with an improved stability.

$R^{29}$ to $R^{38}$ are preferably a hydrogen atom, alkyl group, or phenyl group from the viewpoint of molecular weight. In particular, $R^{30}$ is more preferably a phenyl group, because in that case, the benzene rings contained in general formula (3) are at the meta-positions relative to each other, preventing the triplet energy from decreasing. Here, it is preferably connected to either $L^1$ or $L^2$ in general formula (1-1) given above or either $L^3$ or $L^4$ in general formula (1-2) given above at the position of $R^{32}$. Connection to either $L^1$ or $L^2$ in general formula (1-1) given above or either $L^3$ or $L^4$ in general formula (1-2) given above at the position of any of $R^{29}$ to $R^{38}$ means that one of the carbon atoms connected to $R^{29}$ to $R^{38}$ is connected directly to either $L^1$ or $L^2$ in general formula (1-1) or either $L^3$ or $L^4$ in general formula (1-2). This definition also applies in the following descriptions.

[Chemical formula 8]

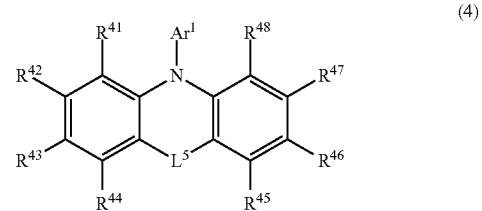

(4)

In the formula, $R^{41}$ to $R^{48}$ may be identical to or different from each other and are selected from the group consisting of a hydrogen atom, alkyl group, cycloalkyl group, heterocyclic ring, amino group, alkenyl group, cycloalkenyl group, alkynyl group, halogen atom, carbonyl group, carboxyl group, oxycarbonyl group, carbamoyl group, silyl group, and $—P(=O)R^{49}R^{50}$. $R^{49}$ and $R^{50}$ represent either an aryl group or a heteroaryl group. $R^{49}$ and $R^{50}$ may be condensed to form a ring. $Ar^1$ denotes a substituted or unsubstituted aryl group or a substituted or unsubstituted heteroaryl group. $L^5$ denotes $CH_2$, $N—Ar^2$, an oxygen atom, or sulfur atom. When $L^5$ is $CH_2$, at least either of the hydrogen atoms may be replaced with an alkyl group. $Ar^2$ denotes a substituted or unsubstituted aryl group or a substituted or unsubstituted heteroaryl group. It is connected to either $L^1$ or $L^2$ in general formula (1-1) given above or either $L^3$ or $L^4$ in general formula (1-2) given above at the position of either any of $R^{41}$ to $R^{48}$ or $Ar^1$.

It is preferable that the two benzene rings bonded to the nitrogen atom be connected to each other via $L^5$ as shown in general formula (4) because the planarity between the benzene rings will increase and the hole transport efficiency will improve.

The group represented by general formula (4) is the dihydroacridinyl group when $L^5$ is $CH_2$, dihydrophenazinyl group when it is $N—Ar^2$, phenoxazinyl group when it is an oxygen atom, and phenothiazinyl group when it is a sulfur atom, of which it is particularly preferably the dihydroacridinyl group because it has the highest electron-donating capacity and acts to improve the hole injection efficiency and hole transport efficiency. When it is the dihydroacridinyl group, furthermore, it is preferable for at least one of the hydrogen atoms in the $CH_2$ of $L^5$ is replaced with an alkyl group because the electron-donating capacity will further increase. It is more preferable that both of the hydrogen atoms be replaced with alkyl groups. Of the various alkyl groups, the methyl group is preferred because of its moderate molecular weight. $Ar^1$ and $Ar^2$ are most preferably aryl groups because of their moderate molecular weights, little electronic influence, and ability to increase the conjugation length, and of the various aryl groups, the phenyl group is more preferable because of a favorable molecular weight.

Connection to either $L^1$ or $L^2$ or either $L^3$ or $L^4$ at the position of any of $R^{41}$ to $R^{48}$ means as described above.

Connection to either $L^1$ or $L^2$ or either $L^3$ or $L^4$ at the position of any of $Ar^2$ means that $L^1$ or the like is connected directly at the position of any element in $Ar^2$. In the case where $Ar^2$ is a phenyl group, for example, $L^1$ or the like is connected directly to one of the carbon atoms existing in the phenyl group. This definition also applies in the following descriptions.

Each of $L^1$ and $L^2$ in general formula (1-1) and $L^3$ and $L^4$ in general formula (1-2) is preferably an arylene group from the viewpoint of synthesis and in particular, it is preferably a phenylene group or a biphenylene group from the viewpoint of molecular weight. In the case where a structure as represented by general formula (4) is connected to these groups, it is preferable that $R^{42}$, $R^{43}$, $R^{46}$, or $R^{47}$ located at the para-position relative to the nitrogen atom in general formula (4) be connected to the para-position of a phenylene group or the para-position of the terminal phenyl group of a biphenylene group because it has an effect of decreasing the ionization potential. Here, $R^{42}$ and $R^{47}$ are at the para-position when $L^5$ is N—$Ar^2$. Furthermore, from the viewpoint of synthesis, it is more preferably connected to $L^1$ in general formula (1-1) or $L^3$ in general formula (1-2).

[Chemical formula 9]

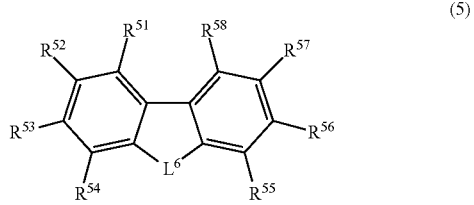

(5)

In the formula, $R^{51}$ to $R^{58}$ may be identical to or different from each other and are selected from the group consisting of a hydrogen atom, alkyl group, cycloalkyl group, aryl group, heterocyclic group, alkenyl group, cycloalkenyl group, alkynyl group, a halogen atom, carbonyl group, carboxyl group, oxycarbonyl group, carbamoyl group, silyl group, and —P(=O)$R^{59}R^{60}$. $R^{59}$ and $R^{60}$ represent an aryl group or a heteroaryl group. $R^{59}$ and $R^{60}$ may be condensed to form a ring. $L^6$ denotes $CH_2$, N—$Ar^3$, an oxygen atom, or sulfur atom. $Ar^3$ denotes a substituted or unsubstituted aryl group or a substituted or unsubstituted heteroaryl group. When $L^6$ is $CH_2$, at least either of the hydrogen atoms may be replaced with an alkyl group. It is connected to either $L^1$ or $L^2$ in general formula (1-1) given above or either $L^3$ or $L^4$ in general formula (1-2) given above at the position of any of $R^{51}$ to $R^{58}$.

It is preferable that the two benzene rings be connected to each other via $L^6$ as shown in general formula (5) because the planarity between the benzene rings will improve and the hole transport efficiency will increase.

The group represented by general formula (5) is the fluorenyl group when $L^6$ is $CH_2$, carbazolyl group when it is N—$Ar^3$, dibenzofuranyl group when it is an oxygen atom, and dibenzothiophenyl group when it is a sulfur atom, of which it is most preferably the fluorenyl group or carbazolyl group because they have a high electron-donating capacity and decrease the ionization potential, leading to an increase in the hole injection efficiency. When it is the fluorenyl group, furthermore, it is preferable for both of the hydrogen atoms in the $CH_2$ of $L^6$ are replaced with alkyl groups, particularly with methyl groups, because the electron-donating capacity will further increase. $Ar^3$ is most preferably an aryl group because of a moderate molecular weight, little electronic influence, and ability to increase the conjugation length, and of the various aryl groups, the phenyl group is more preferable because of a favorable molecular weight. Connection to either $L^1$ or $L^2$ in general formula (1-1) given above or either $L^3$ or $L^4$ in general formula (1-2) given above at the position of any of $R^{51}$ to $R^{58}$ means as described above.

Each of $L^1$ and $L^2$ in general formula (1-1) and $L^3$ and $L^4$ in general formula (1-2) is preferably an arylene group from the viewpoint of synthesis and in particular, it is preferably a phenylene group or biphenylene group from the viewpoint of molecular weight. In the case where a structure as represented by general formula (5) is connected to these groups, it is preferable that $R^{52}$ or $R^{57}$ located at the para-position relative to the heteroatom in general formula (5) be connected to the para-position of a phenylene group or the para-position of the terminal phenyl group of a biphenylene group because it has an effect of decreasing the ionization potential. Here, $R^{52}$ and $R^{57}$ are at the para-position relative to the heteroatom when $L^6$ is not $CH_2$. Furthermore, from the viewpoint of synthesis, it is more preferably connected to $L^1$ in general formula (1-1) or $L^3$ in general formula (1-2).

[Chemical formula 10]

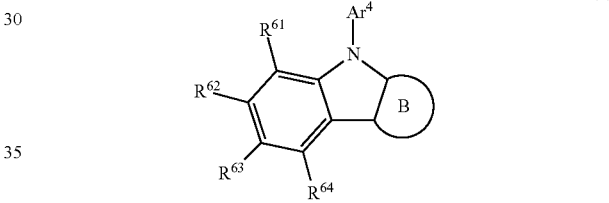

(6)

In the formula, ring B represents a substituted or unsubstituted condensed aromatic hydrocarbon ring, substituted or unsubstituted monocyclic aromatic heterocyclic ring, or substituted or unsubstituted condensed aromatic heterocyclic ring. In the formula, $R^{61}$ to $R^{64}$ may be identical to or different from each other and are selected from the group consisting of a hydrogen torn, alkyl group, cycloalkyl group, heterocyclic group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group, carbamoyl group, silyl group, and —P(=O)$R^{65}R^{66}$. $R^{65}$ and $R^{66}$ represent an aryl group or a heteroaryl group. $R^{65}$ and $R^{66}$ may be condensed to form a ring. $Ar^4$ denotes a substituted or unsubstituted aryl group or a substituted or unsubstituted heteroaryl group. It is connected to either $L^1$ or $L^2$ in general formula (1-1) given above or either $L^3$ or $L^4$ in general formula (1-2) given above at the position of any of $R^{61}$ to $R^{64}$, $Ar^4$, and ring B.

It is preferable that the benzene ring bonded to the nitrogen atom and ring B be connected to each other to form a ring-fused structure as in general formula (6) because the planarity between the benzene ring and ring B will increase and the hole transport efficiency will improve. In particular, it is preferable for ring B to have a structure as represented by any of general formulae (A) to (D) given below. A high carrier mobility will be developed if ring B has a structure as represented by any of general formulae (A) to (D) given below. As a result, a light emitting device of a low driving voltage can be obtained, leading to an improved luminous efficiency. Furthermore, a film with improved stability will be obtained as a result of sublimability, deposition stability, decreased crystallinity, and increased glass transition temperature. These structures may further contain a substituent group, but in such a case, it is preferable for the substituent group to be the methyl group from the viewpoint of molecular weight. From the viewpoint of synthesis, the structures of these general formulae are preferably connected at the position of $L^1$ in general formula (1-1) or at the position of $L^3$ in general formula (1-2).

[Chemical formula 11]

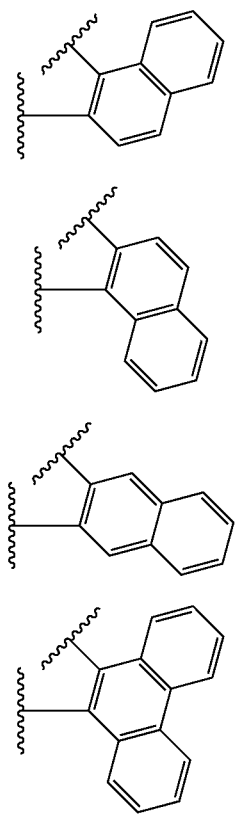

Ar$^4$ is most preferably an aryl group because of a moderate molecular weight, little electronic influence, and ability to increase the conjugation length, and of the various aryl groups, the phenyl group is more preferable because of a favorable molecular weight. Connection to either $L^1$ or $L^2$ in general formula (1-1) given above or either $L^3$ or $L^4$ in general formula (1-2) given above at the position of any of $R^{61}$ to $R^{64}$ and Ar$^4$ means as described above. Connection to either $L^1$ or $L^2$ or either $L^3$ or $L^4$ at the position of ring B means that $L^1$ or the like is connected directly to the position of any element in ring B. In the case where ring B is a benzene ring, for example, $L^1$ or the like is connected directly to one of the carbon atoms existing in the benzene ring. This definition also applies in the following descriptions.

Each of $L^1$ and $L^2$ in general formula (1-1) and $L^3$ and $L^4$ in general formula (1-2) is preferably an arylene group from the viewpoint of synthesis and in particular, it is preferably a phenylene group or a biphenylene group from the view-point of molecular weight. In the case where a structure as represented by general formula (6) is connected to these groups, it is preferable that $R^{63}$ located at the para-position relative to the nitrogen atom in general formula (6) be connected to the para-position of a phenylene group or the para-position of the terminal phenyl group of a biphenylene group because it has an effect of decreasing the ionization potential. Furthermore, from the viewpoint of synthesis, it is more preferable for $R^{63}$ in general formula (6) to be connected to $L^1$ in general formula (1-1) or $L^3$ in general formula (1-2).

[Chemical formula 12]

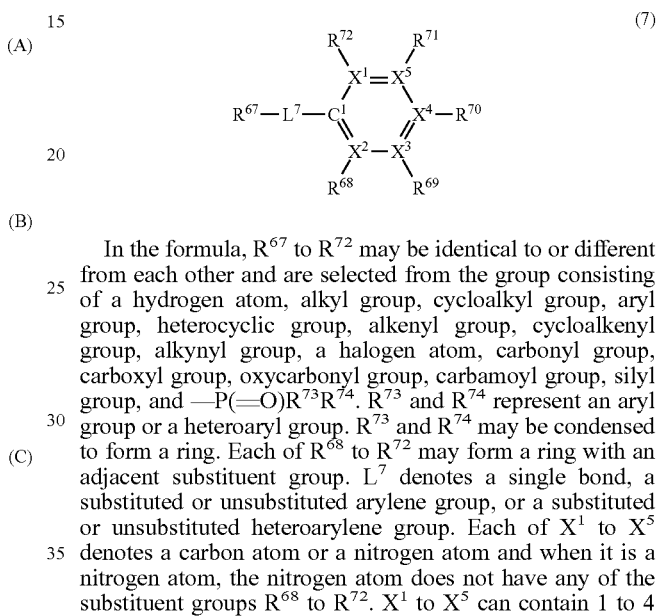

In the formula, $R^{67}$ to $R^{72}$ may be identical to or different from each other and are selected from the group consisting of a hydrogen atom, alkyl group, cycloalkyl group, aryl group, heterocyclic group, alkenyl group, cycloalkenyl group, alkynyl group, a halogen atom, carbonyl group, carboxyl group, oxycarbonyl group, carbamoyl group, silyl group, and —P(=O)R$^{73}$R$^{74}$. R$^{73}$ and R$^{74}$ represent an aryl group or a heteroaryl group. R$^{73}$ and R$^{74}$ may be condensed to form a ring. Each of R$^{68}$ to R$^{72}$ may form a ring with an adjacent substituent group. L$^7$ denotes a single bond, a substituted or unsubstituted arylene group, or a substituted or unsubstituted heteroarylene group. Each of X$^1$ to X$^5$ denotes a carbon atom or a nitrogen atom and when it is a nitrogen atom, the nitrogen atom does not have any of the substituent groups R$^{68}$ to R$^{72}$. X$^1$ to X$^5$ can contain 1 to 4 nitrogen atoms. However, it is connected to either L$^1$ or L$^2$ in general formula (1-1) given above or either L$^3$ or L$^4$ in general formula (1-2) given above at the position of R$^{67}$. C$^1$ denotes a carbon atom.

If a group containing a nitrogen atom is substituted in a 6-membered ring as represented by general formula (7), the electronic affinity of the molecule will increase, leading to an improved electron injection efficiency. Accordingly, it will be suitable for use particularly in light emitting layers that require high carrier transport efficiency for both holes and electrons.

From the viewpoint of molecular weight, it is preferable for L$^7$ to be a single bond, phenylene group, or pyridylene group. If, of the groups of X$^1$ to X$^5$, the three of X$^1$, X$^2$, and X$^4$ are nitrogen atoms, the 6-membered ring will form a triazine backbone, which is particularly preferred because of high electronic affinity and easy electron injection. Each of R$^{68}$ to R$^{72}$ may form a ring with an adjacent substituent group and preferable examples of such a structure include the following.

[Chemical formula 13]

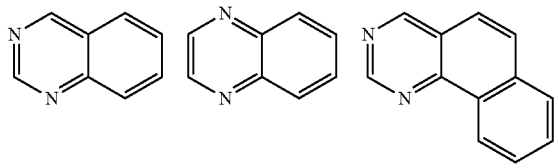

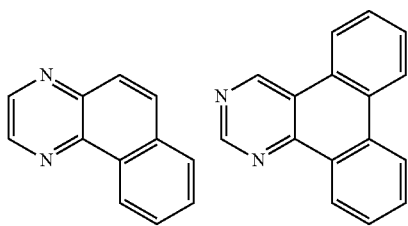
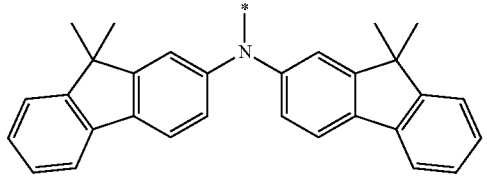

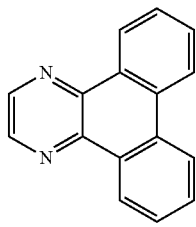
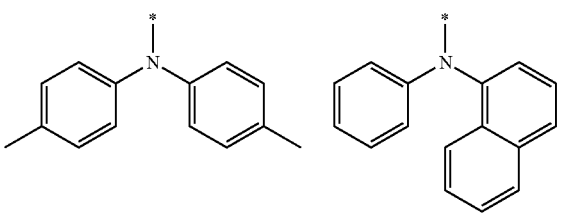

These structures may further contain a substituent group, but in such a case, it is preferable for the substituent group to be the methyl group from the viewpoint of molecular weight. Connection to either $L^1$ or $L^2$ in general formula (1-1) given above or either $L^3$ or $L^4$ in general formula (1-2) given above at the position of $R^{67}$ means as described above.

There are no specific limitations on the groups represented by general formulae (2) to (7), but specific examples include the following.

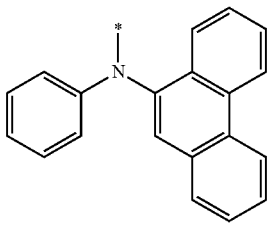

[Chemical formula 14]

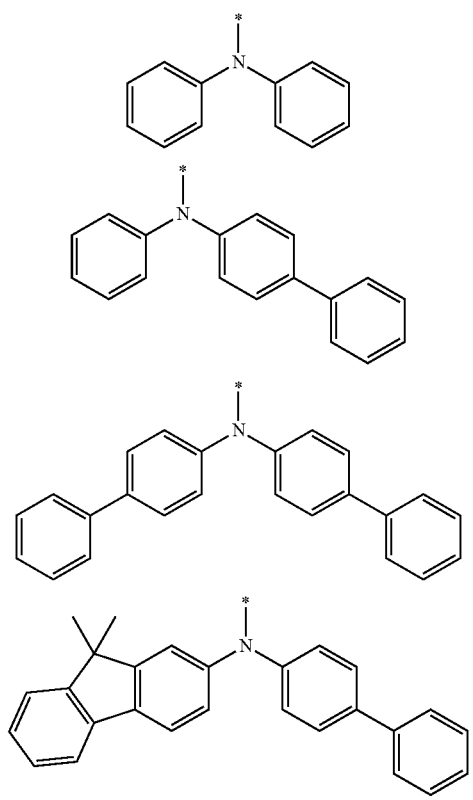
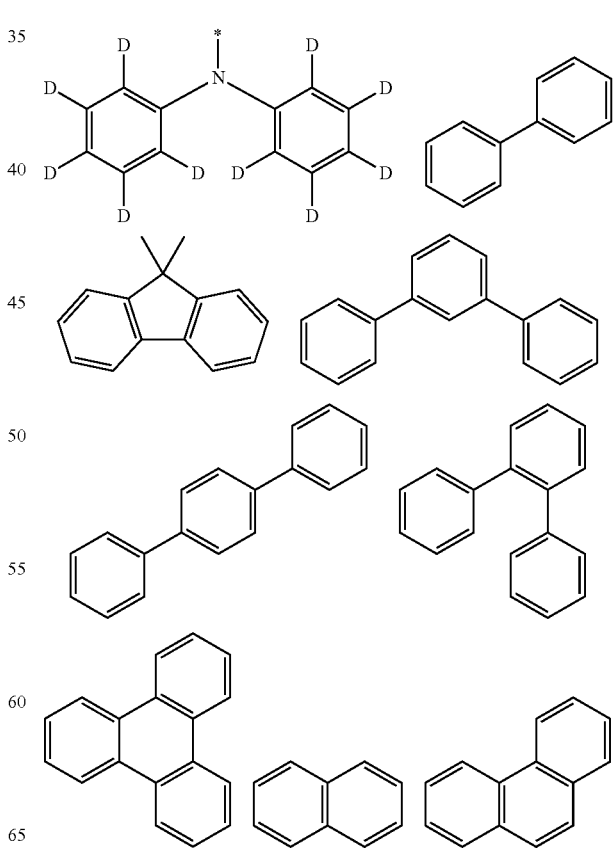

[Chemical formula 15]
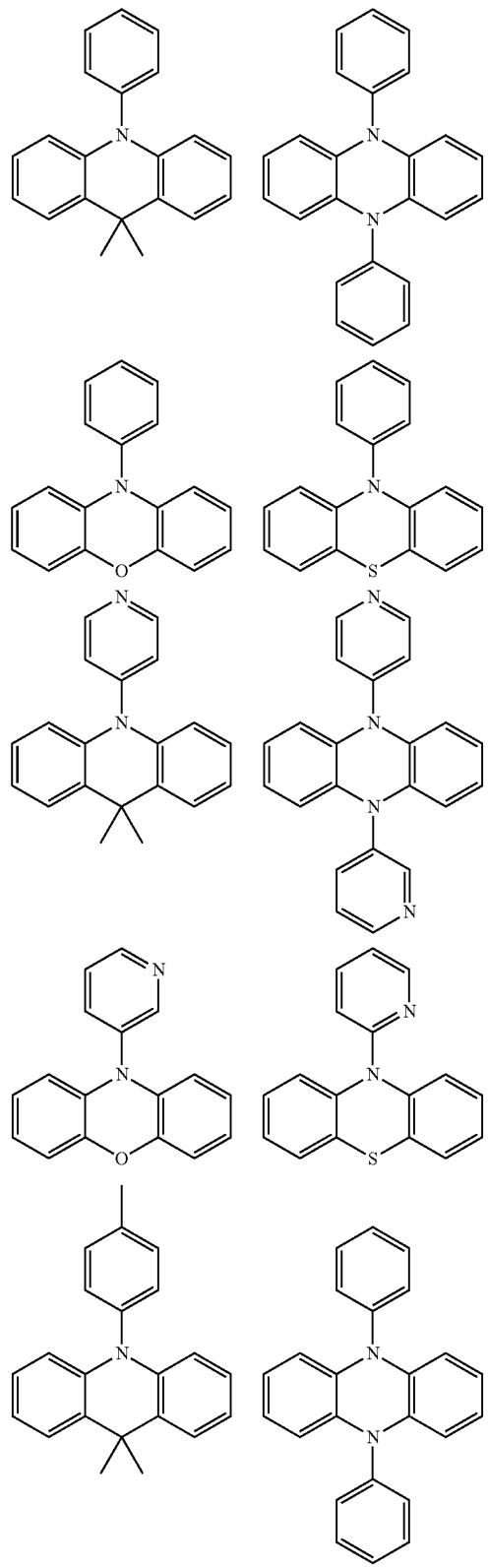
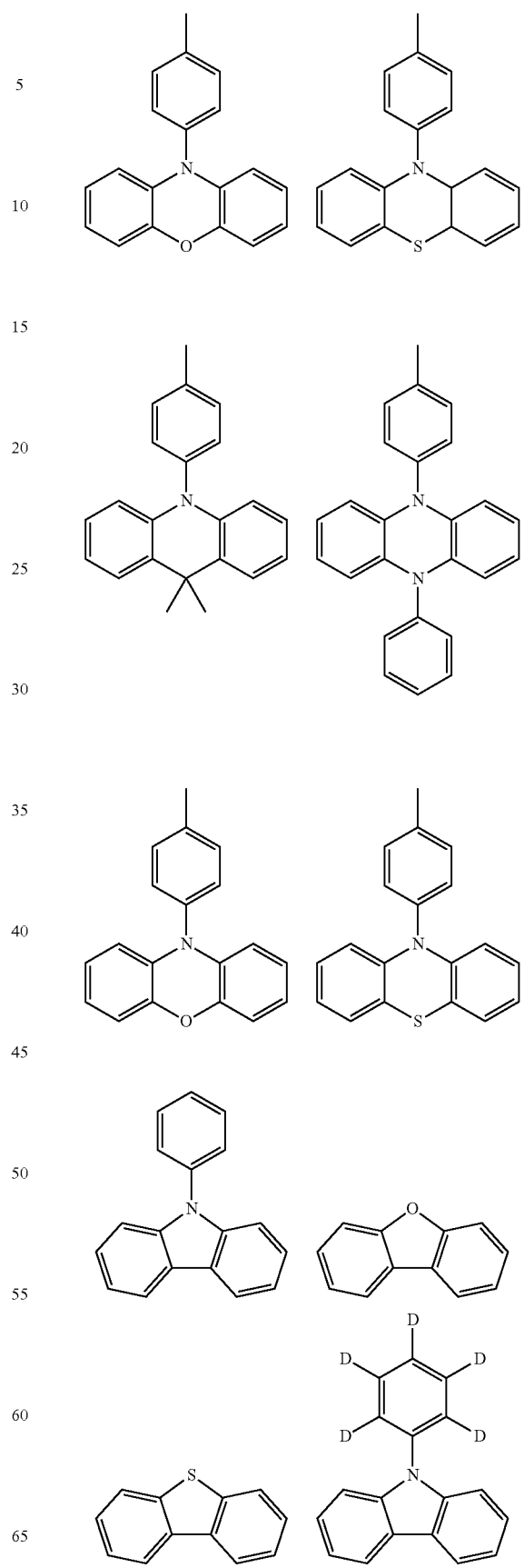

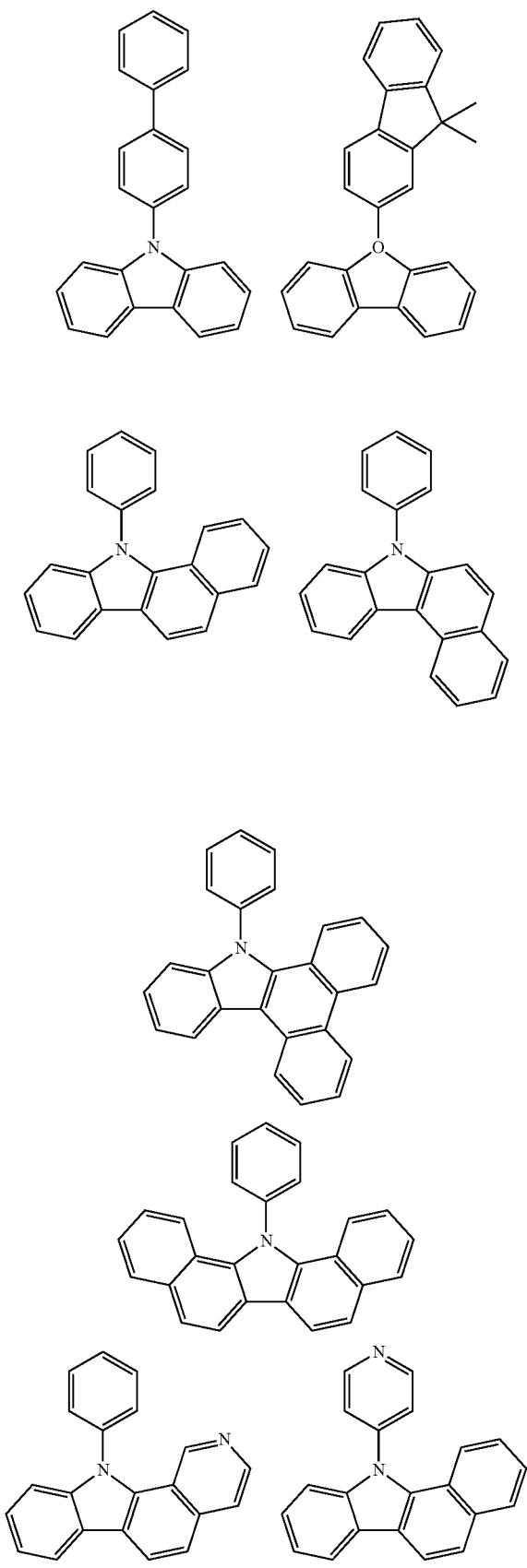
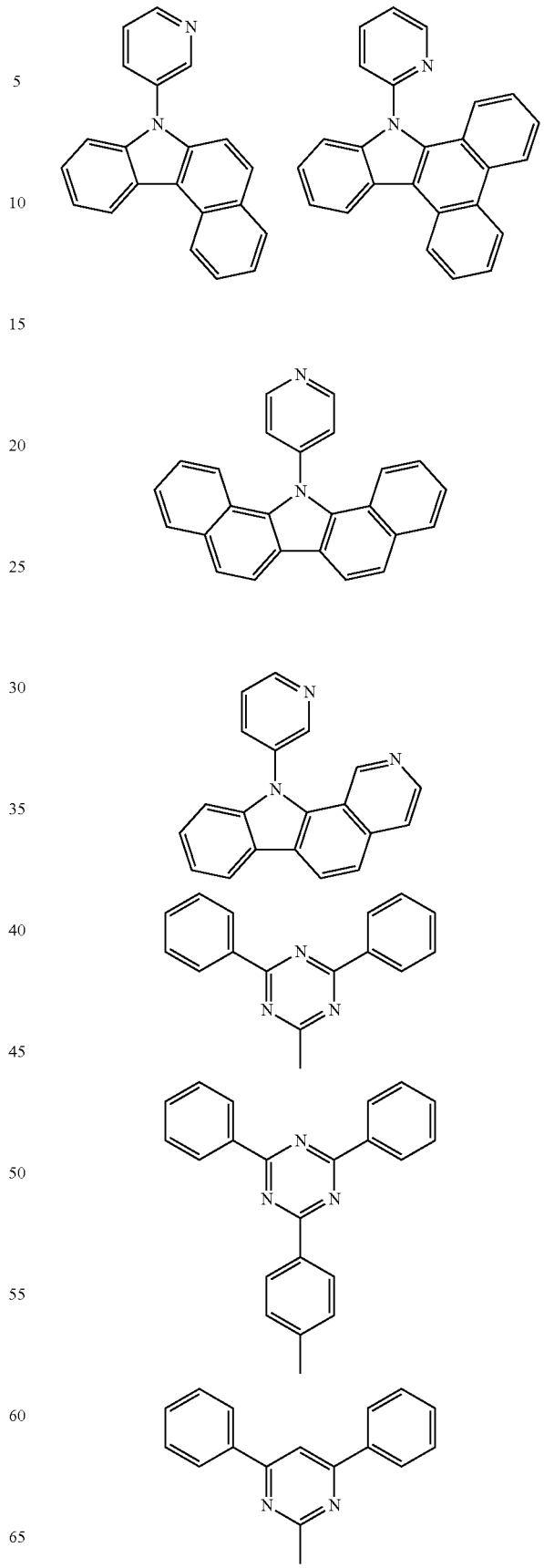

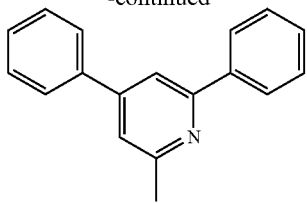

In view of the material availability and synthesis cost, it is most preferable for all of $R^1$ to $R^{24}$ to be hydrogen atoms. In the case where not all of $R^1$ to $R^{24}$ are hydrogen atoms, it is preferable for them to be alkyl groups, cycloalkyl groups, or alkoxy groups because these groups do not have a significant influence on decreasing the triplet level or increasing the ionization potential. These groups may be further substituted.

There are no specific limitations on the benzindolocarbazole derivatives represented by general formula (1-1) or (1-2), but specific examples include the following. It should be noted that these are only examples and compounds other than those listed here may be used favorably if they have structures as represented by general formula (1-1) or (1-2).

[Chemical formula 16]

[1]
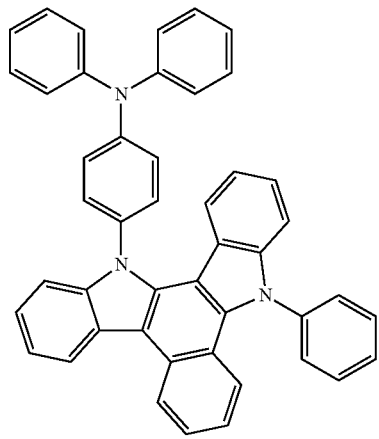

[2]
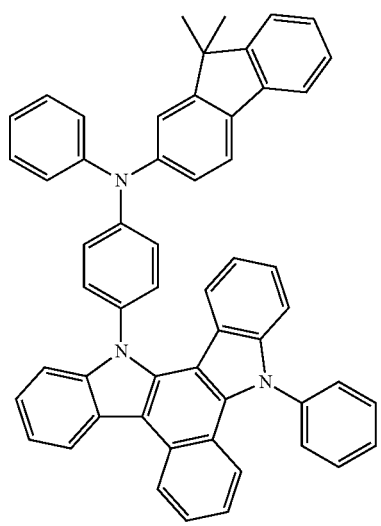

[3]
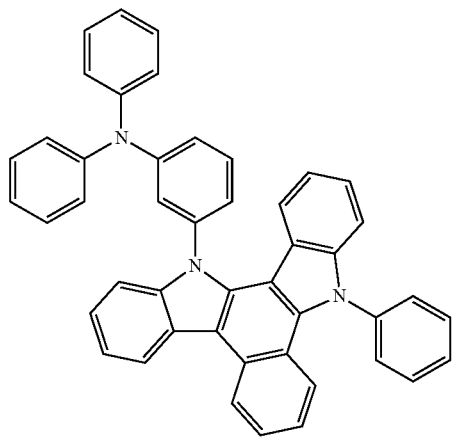

[4]
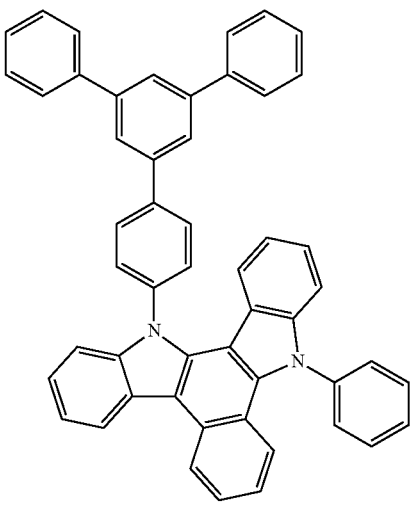

[5]
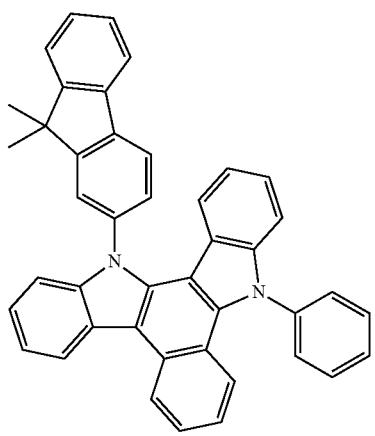

[6]
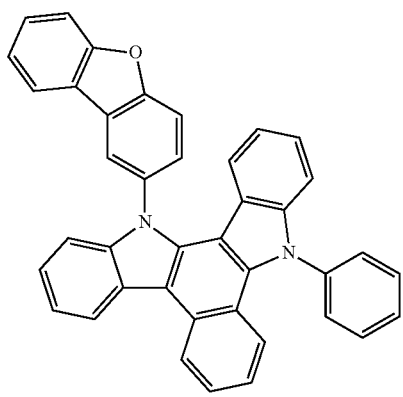
[7]
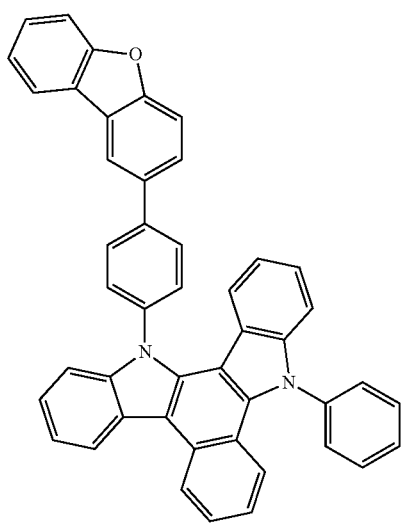
[8]
[9]
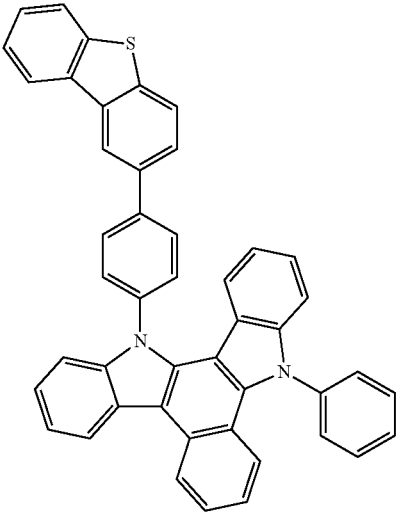
[10]
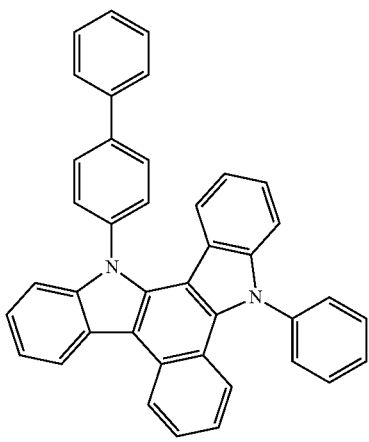
[11]
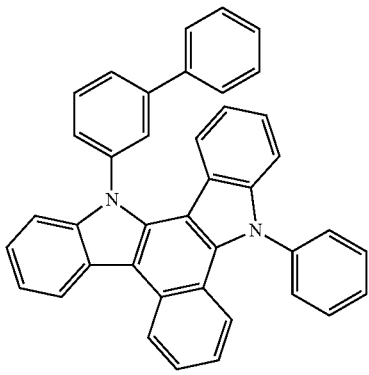

[12]
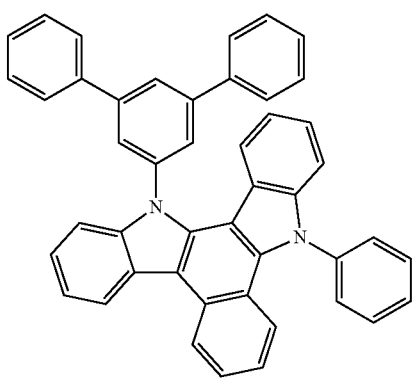
[Chemical formula 17]
[13]
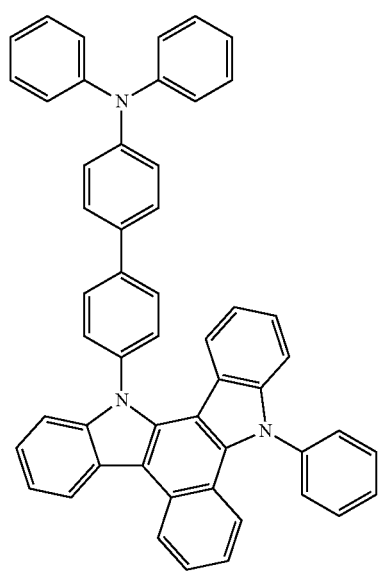
[14]
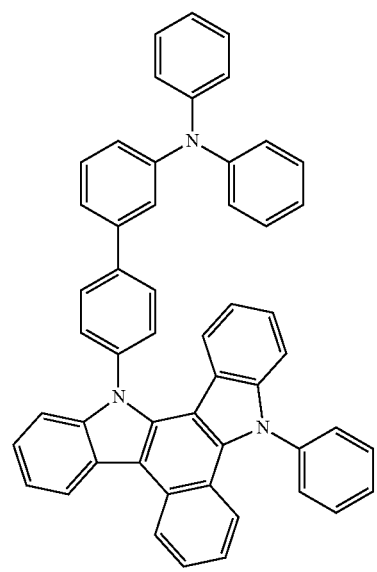
[15]
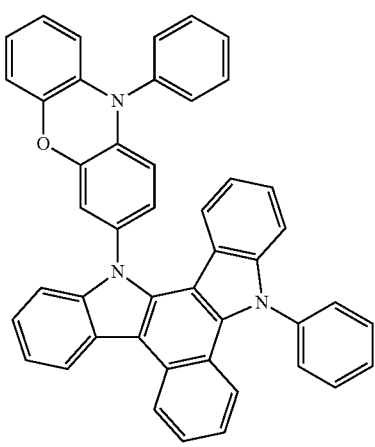
[16]
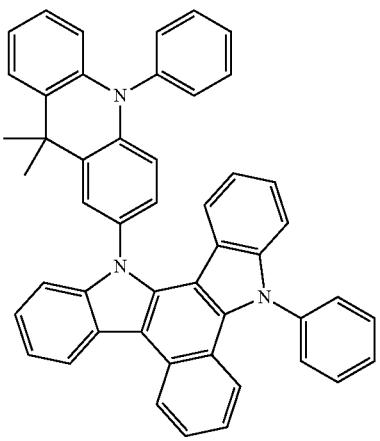
[17]
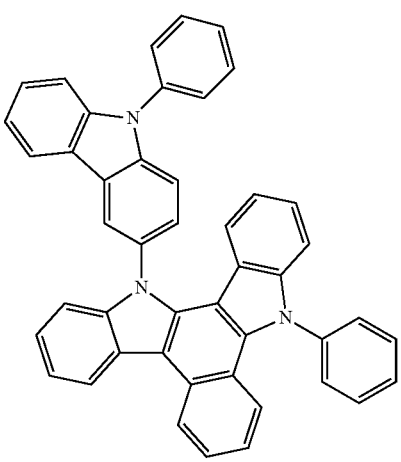

[18]
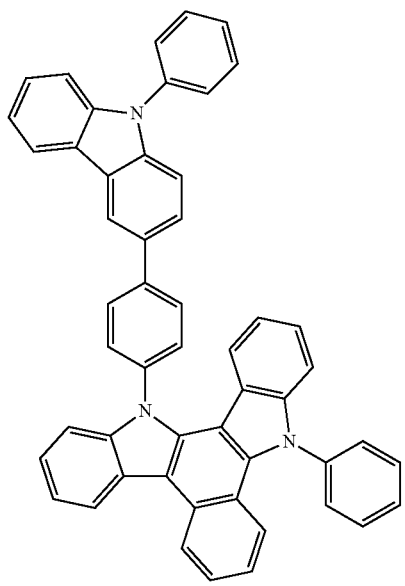
[19]
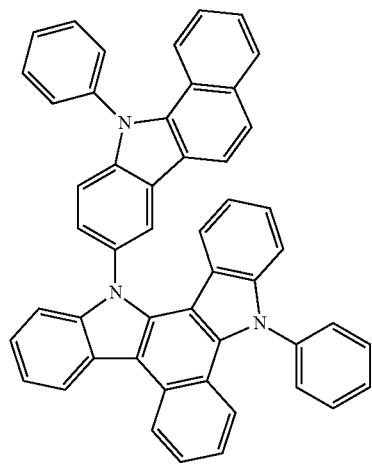
[20]
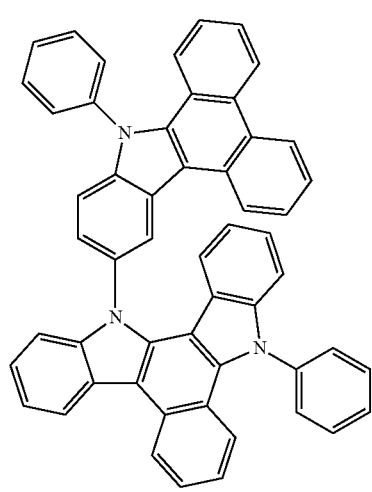
[21]
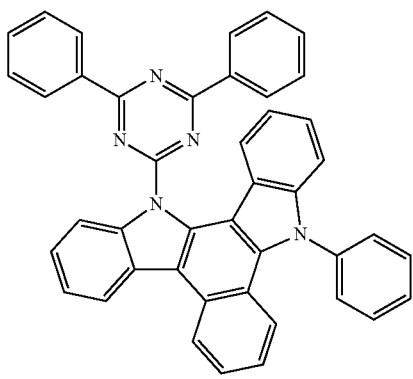
[22]
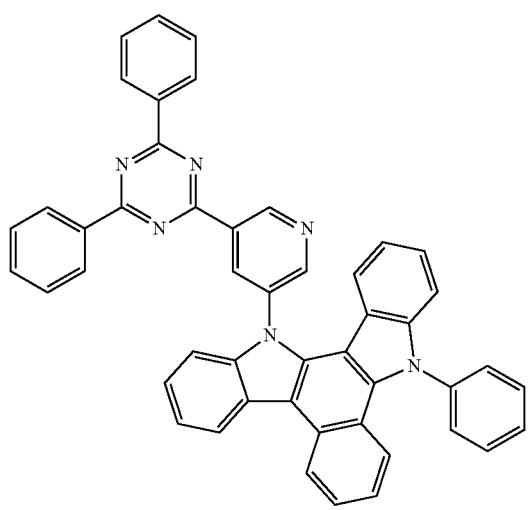
[23]
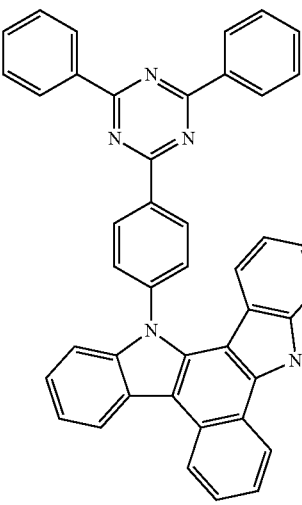

[24]
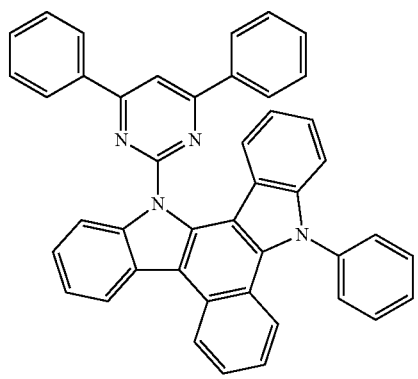
[Chemical formula 18]
[25]
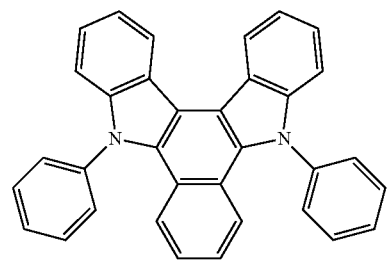
[26]
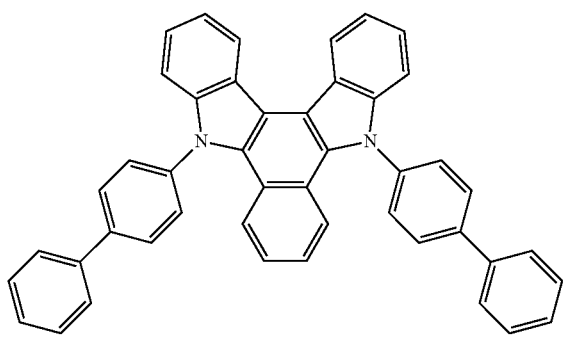
[27]
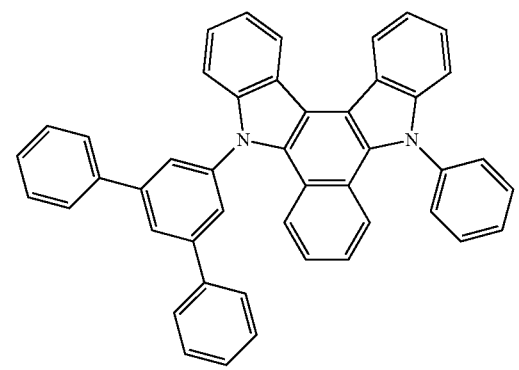
[28]
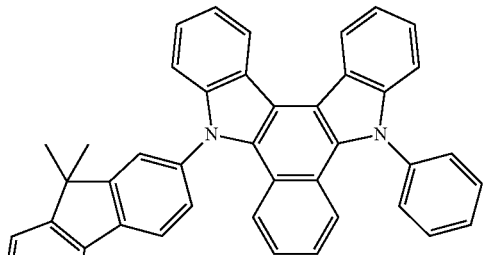
[29]
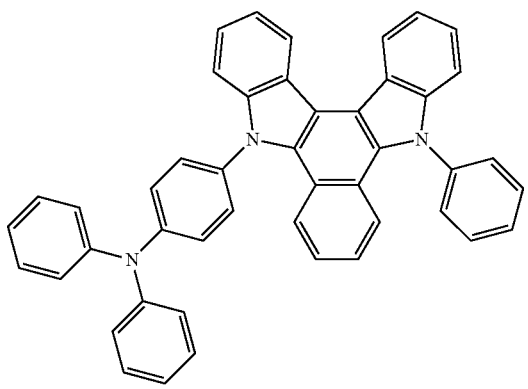
[30]
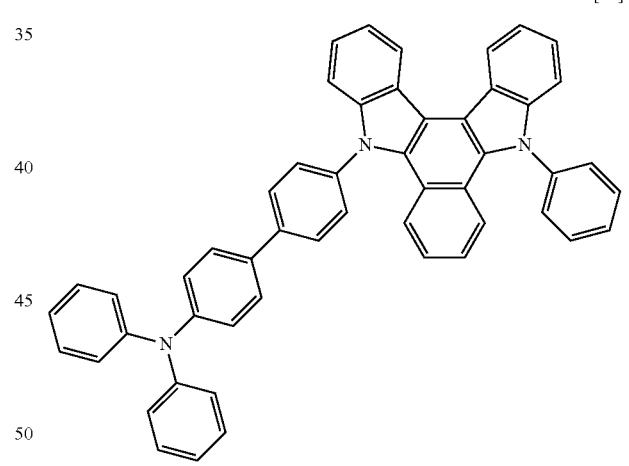
[31]
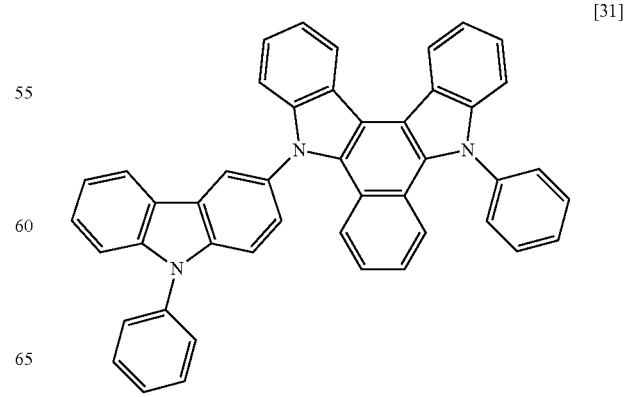

[32]
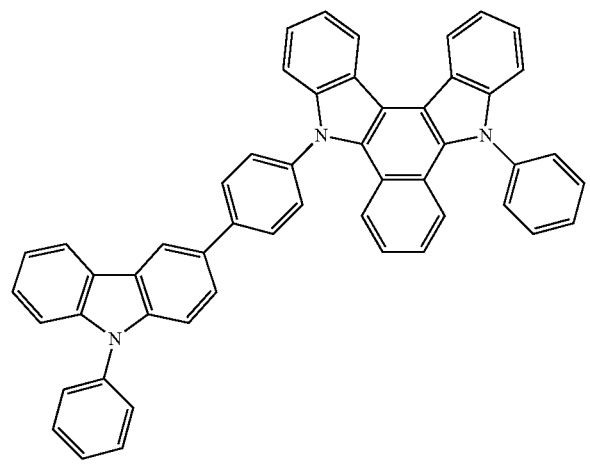
[33]
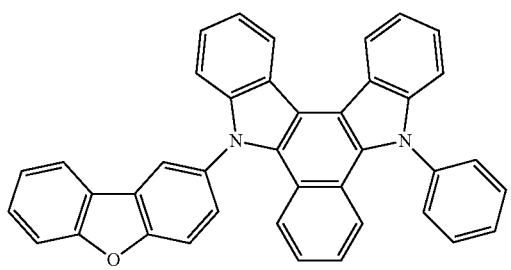
[34]
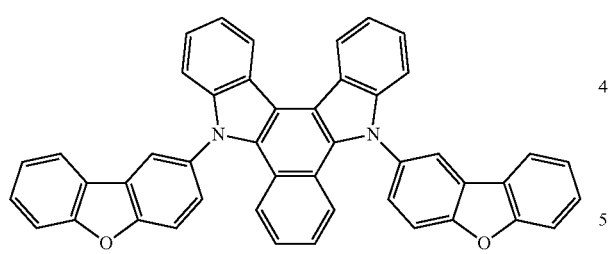
[35]
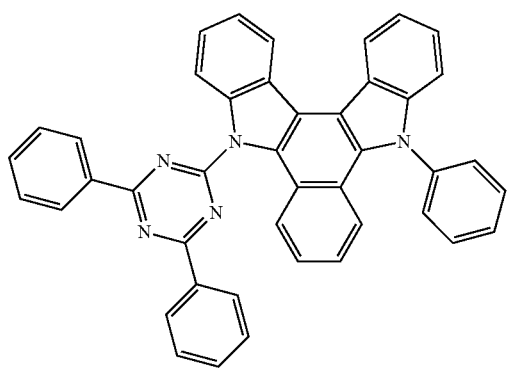
[36]
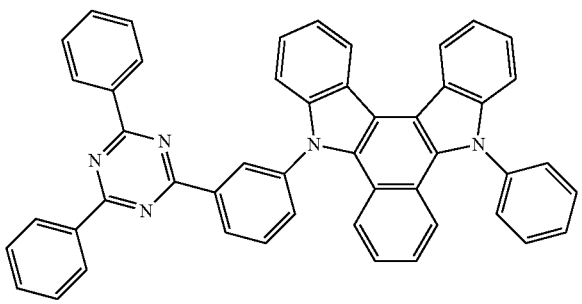
[Chemical formula 19]
[37]
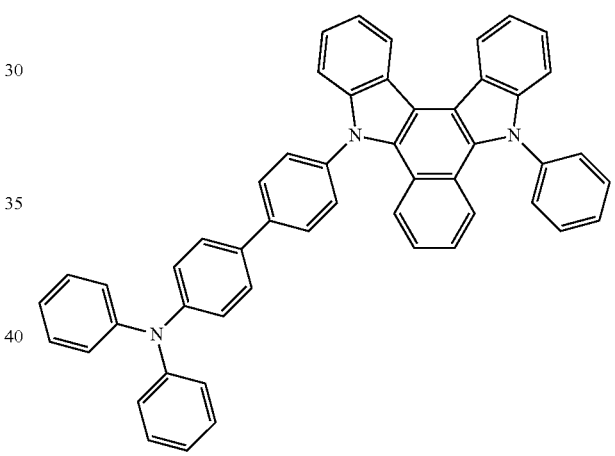
[39]
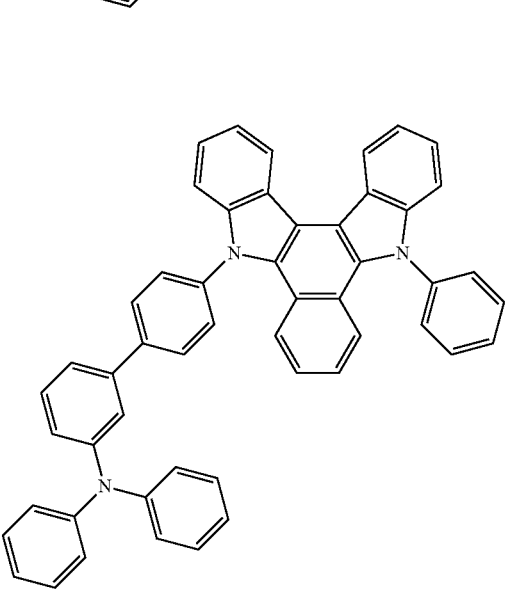

[40]
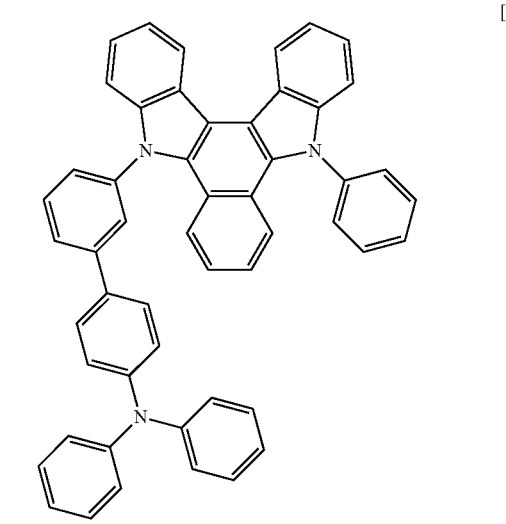
[41]
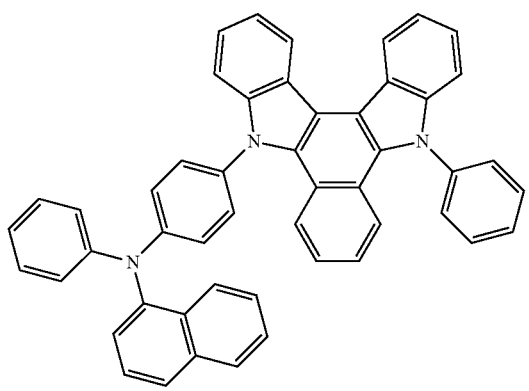
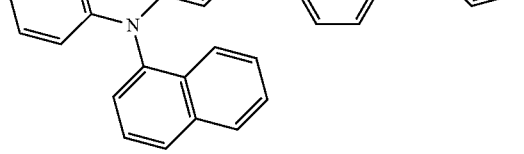
[42]
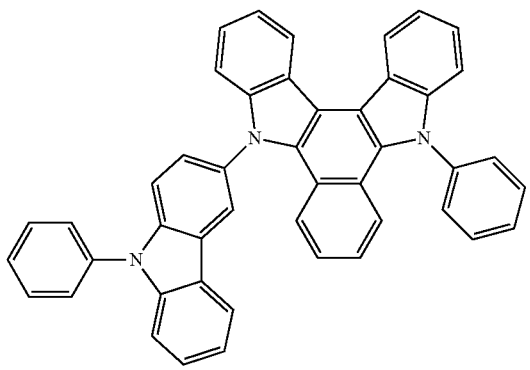
[43]
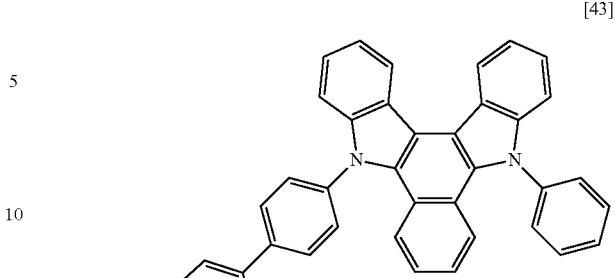
[44]
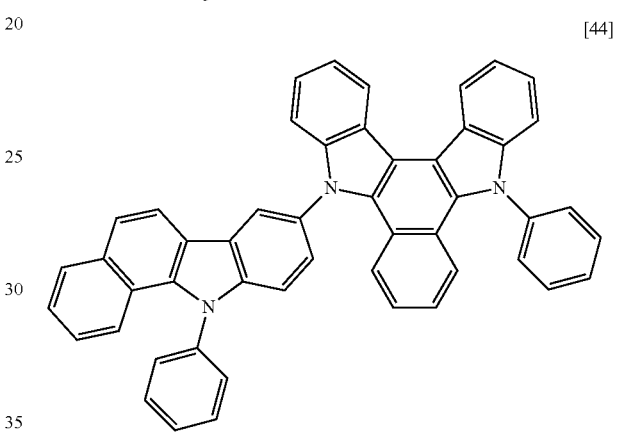
[45]
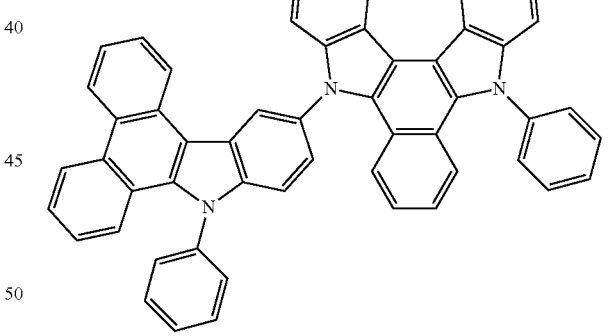
[46]
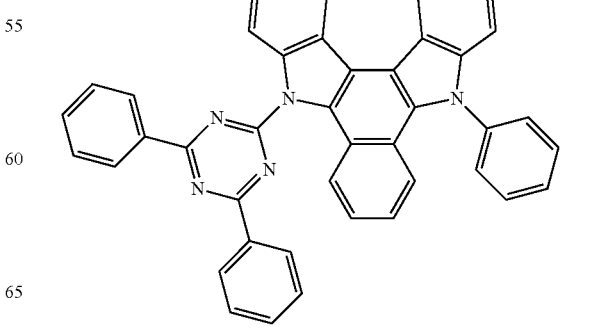

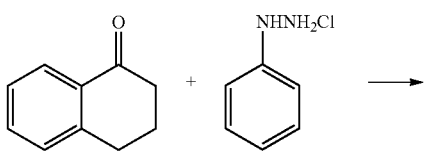

[Chemical formula 20]

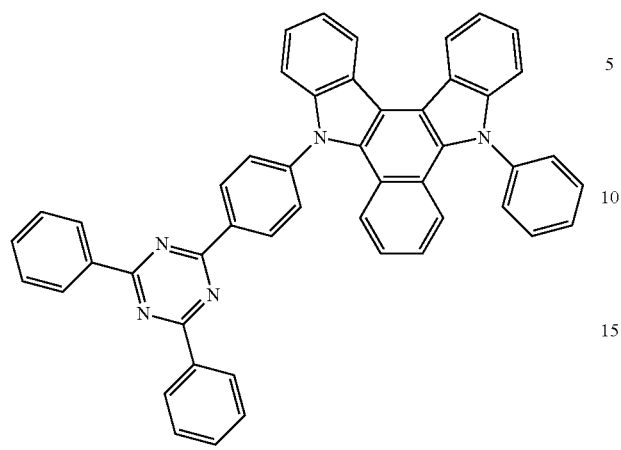

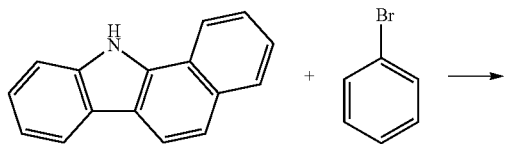

intermediate A

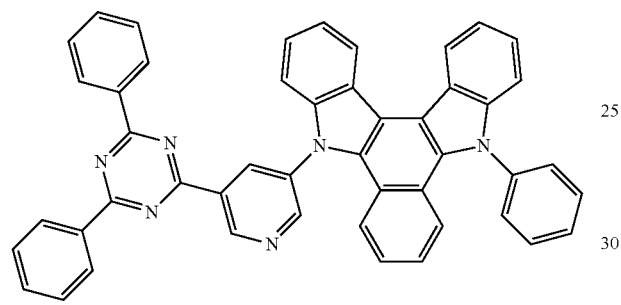

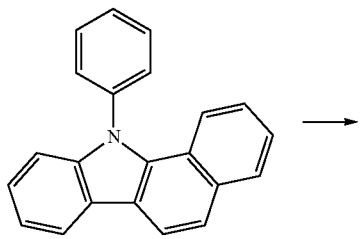

intermediate B

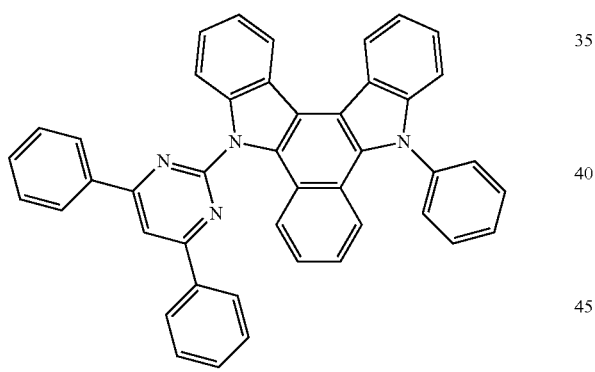

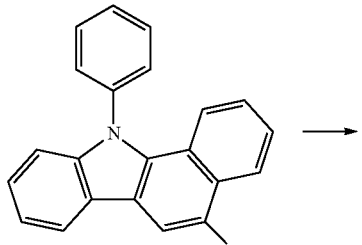

intermediate C

Compounds having benzindolocarbazole backbones as listed above can be synthesized using generally known methods. For example, a method available for synthesizing benzindolocarbazole is to subjecting a boronic ester, i.e. a benzocarbazole derivative produced with a palladium or copper catalyst, and halogenated nitro benzene to the Suzuki coupling reaction and then reacting the resulting product in a solvent with a high boiling point such as orthodichlorobenzene using a catalyst, although the present invention is not limited to this.

For example, a method available for introducing a substituent group onto the nitrogen atom in benzindolocarbazole is to perform coupling reaction of a benzindolocarbazole derivative and a halide using a palladium or copper catalyst, although the present invention is not limited to this. An example of these methods which uses 11-phenyl-5-(4,4,5,5-tetramethyl-1,3,2-dioxaborolan-2-yl)-11H-benzo[a]carbazole (intermediate D) and 5-phenyl-5,14-dihydrobenzo[a]indolo[3,2-c]carbazole (intermediate F) is shown below.

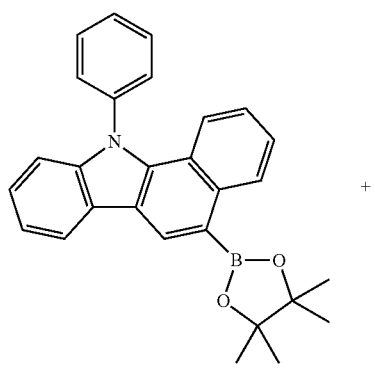

intermediate D

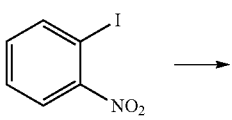

-continued

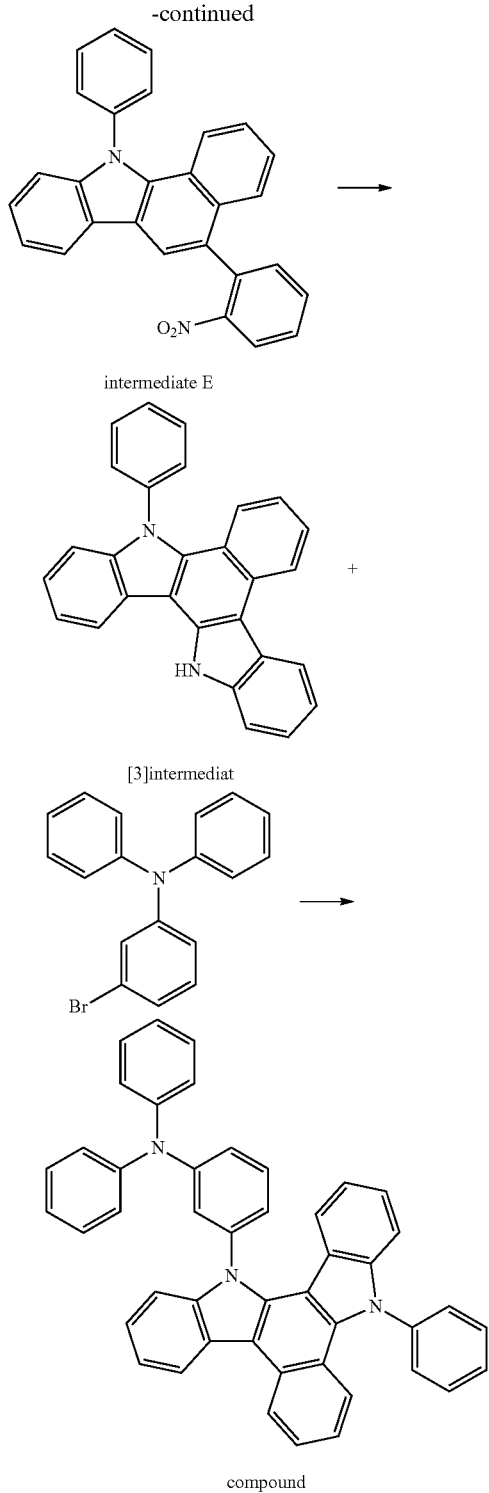

intermediate E

[3]intermediat compound

Benzindolocarbazole derivatives as represented by general formula (1-1) or (1-2) are used favorably as light emitting device material. Here, a light emitting device material as referred to for the present invention is one used to form any layer in a light emitting device and such materials include those used to form a hole injection layer, hole transport layer, light emitting layer, and/or electron transport layer and also those used to form a cathode protection film. A light emitting device having both high luminous efficiency and high durability can be obtained by using a benzindolocarbazole derivative as represented by general formula (1-1) or (1-2) to form a layer in a light emitting device.

An embodiment of the light emitting device according to the present invention is described in detail below. The light emitting device according to the present invention contains an anode, cathode, and an organic layer interposed between the anode and the cathode, and the organic layer works to convert electric energy for light emission.

Examples of the layer structure between the anode and the cathode in the light emitting device include, in addition to the use of a light emitting layer alone, the following: 1) light emitting layer/electron transport layer, 2) hole transport layer/light emitting layer, 3) hole transport layer/light emitting layer/electron transport layer, 4) hole injection layer/hole transport layer/light emitting layer/electron transport layer, 5) hole transport layer/light emitting layer/electron transport layer/electron injection layer, 6) hole injection layer/hole transport layer/light emitting layer/electron transport layer/electron injection layer. Each of the above layers may be a single layer or composed of a plurality of layers and they may be or may not be doped.

Benzindolocarbazole derivatives as represented by general formula (1-1) or (1-2) may be used in any of the above layers in a light emitting device, but they may be used particularly favorably in the hole transport layer.

In the light emitting device according to the present invention, the anode and the cathode play a role in supplying a sufficient electric current to allow the device to emit light and it is desirable for at least either of them to be transparent or translucent to extract light therethrough. Commonly, a transparent anode is formed on the substrate.

There are no specific limitations on the material used to form the anode as long as it serves to allow holes to be injected into an organic layer efficiently and is transparent or translucent to allow light to be extracted therethrough. Useful ones include electrically conductive metal oxides such as zinc oxide, tin oxide, indium oxide, indium tin oxide (ITO), and indium zinc oxide (IZO); metals such as gold, silver, and chromium; inorganic electrically conductive substances such as copper iodide and copper sulfide; and electrically conductive polymers such as polythiophene, polypyrrole, and polyaniline; and the use of ITO glass and NESA glass is particularly preferable. Each of these electrode materials may be used singly or a plurality of these materials may be used in the form of stacked layers or a mixture. There are no specific limitations on the resistance of the transparent electrode as long as it can supply a sufficiently large electric current required to allow the device to emit light, but it is desirable for the resistance to be low from the viewpoint of the electric power consumption of the device. For example, an ITO substrate of 300Ω/□ or less can work as an electrode for a device, but substrates of about 10Ω/□ are available these days and accordingly, the use of a substrate with a low resistance of 20Ω/□ or less is particularly desirable. The thickness of the ITO layer may be adjusted appropriately to suit the resistance, but commonly it is in the range of 45 to 300 nm.

Furthermore, it is preferable for the light emitting device to have a substrate for support thereof in order to allow the light emitting device to maintain a required mechanical strength. Preferable substrate materials include glass materials such as soda glass and alkali-free glass. The thickness of the glass substrate may be as small as 0.5 mm or more as long as it is thick enough to maintain a required mechanical strength. With respect to the glass material, the use of alkali-free glass is preferable because it does not suffer significant ion elution. In addition, soda lime glass with a barrier coat of $SiO_2$ is now commercially available and this may be used. As long as the first electrode can function stably, furthermore, the substrate is not necessarily of a glass material and for example, an anode may be formed on a plastic substrate. There are no specific limitations on the method used for ITO film formation and useful ones include the electron beam method, sputtering method, and chemical reaction method.

There are no specific limitations on the material of the cathode as long as the material allows electrons to be injected into the light emitting layer efficiently. Generally, preferable ones include metals such as platinum, gold, silver, copper, iron, tin, aluminum, and indium; and alloys and multilayer laminates formed of the former with a metal with a low work function such as lithium, sodium, potassium, calcium, and magnesium. In particular, their primary component is preferably aluminum, silver, or magnesium from the viewpoint of electric resistance, easiness of film production, film stability, and luminous efficiency. In particular, it is preferably formed mainly of magnesium and silver because electrons can be injected easily into the electron transport layer and electron injection layer according to the present invention to permit driving at a low voltage.

To protect the cathode, furthermore, it is preferable to coat the cathode with a protective film layer formed of a metal such as platinum, gold, silver, copper, iron, tin, aluminum, and indium, an alloy thereof, an inorganic substance such as silica, titania, and silicon nitride; or an organic polymer compound such as polyvinyl alcohol, polyvinyl chloride, hydrocarbon based polymers. In the case of a device structure where light is extracted through the cathode (top emission structure), however, the protective film layer to be adopted is formed of a material that is optically transparent in the visible light region. There are no specific limitations on the method used to produce these electrodes, and useful ones include resistance heating, electron beam, sputtering, ion plating, and coating.

The hole injection layer is located between the anode and the hole transport layer. The hole injection layer may be a single layer or a stack of plurality of layers. The existence of the hole injection layer between the hole transport layer and the anode is preferable because this allows driving at a low voltage and an increase in durable life and furthermore, the device will have an improved carrier balance, leading to an increased luminous efficiency.

There are no specific limitations on the material used for the hole injection layer and examples include benzidine derivatives such as 4,4'-bis(N-(3-methylphenyl)-N-phenylamino) biphenyl (TPD), 4,4'-bis(N-(1-naphthyl)-N-phenylamino) biphenyl (NPD), 4,4'-bis(N,N-bis(4-biphenylyl) amino) biphenyl (TBDB), and bis(N,N'-diphenyl-4-aminophenyl)-N,N-diphenyl-4,4'-diamino-1,1'-biphenyl (TPD232); materials that are called starburst arylamines such as 4,4',4''-tris-(3-methylphenyl(phenyl)amino)triphenylamine (m-MTDATA), and 4,4',4''-tris-(1-naphthyl(phenyl)amino)triphenylamine (1-TNATA); biscarbazole derivatives such as bis(N-arylcarbazole) and bis(N-alkylcarbazole); heterocyclic compounds such as pyrazoline derivatives, stilbene based compounds, hydrazine based compounds, benzofuran derivatives, thiophene derivatives, oxadiazole derivatives, phthalocyanine derivatives, and porphyrin derivatives; and polymers such as polycarbonates and styrene derivatives containing any of the above-mentioned monomers in side chains as well as polythiophene, polyaniline, polyfluorene, polyvinyl carbazol, and polysilane. In addition, compounds as represented by general formula (1-1) or (1-2) can also be used. Among others, benzidine derivatives and starburst arylamine based materials are preferred because they have a lower HOMO level than the compounds represented by general formula (1-1) or (1-2) and work more smoothly in injecting and transporting holes from the anode into the hole transport layer.

Each of these materials may be used singly or as a combination of a plurality of the materials. Or, a plurality of the materials may be stacked to form a hole injection layer. It is preferable, furthermore, that this hole injection layer be formed only of an acceptor type compound or formed of a hole-injecting material as given above that is doped with an acceptor type compound because the effect described above will be further enhanced. An acceptor type compound as referred to herein is defined as one that forms a charge transfer complex with the hole transport layer in the case where the compound is used in the form of a monolayer film or with the material that constitutes the hole injection layer in the case where it is used as a dopant. The use of such a material serves to improve the electric conductivity of the hole injection layer and contributes to decreasing the driving voltage of the device, leading to an improved luminous efficiency and improved durable life.

Examples of such acceptor type compounds include metal chlorides such as iron (III) chloride, aluminum chloride, gallium chloride, indium chloride, and antimony chloride; metal oxides such as molybdenum oxide, vanadium oxide, tungsten oxide, and ruthenium oxide; and charge transfer complexes such as tris-(4-bromophenyl) aminium hexachloroantimonate (TBPAH). Others that are also used favorably include organic compounds having a nitro group, cyano group, halogen atom, or trifluoromethyl group in a molecule as well as quinone based compounds, anhydride based compounds, and fullerene. Specific examples of such compounds include hexacyanobutadiene, hexacyanobenzene, tetracyanoethylene, tetracyanoquinodimethan (TCNQ), tetrafluorotetracyanoquinodimethan (F4-TCNQ), radialene derivative, p-fluoranil, p-chloranil, p-bromanil, p-benzoquinone, 2,6-dichlorobenzoquinone, 2,5-dichlorobenzoquinone, tetramethyl benzoquinone, 1,2,4,5-tetracyanobenzene, o-dicyanobenzene, p-dicyanobenzene, 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphthoquinone, 2,3-dichloronaphthoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic anhydride, phthalic anhydride, C60, and C70.

Of these, metal oxides and cyano-containing compounds are preferred because they can be handled easily and deposited easily, allowing the effects described above to develop easily. Regardless of whether the hole injection layer is formed only of an acceptor type compound or the hole injection layer is doped with an acceptor type compound, the hole injection layer may be a monolayer or a stack of a plurality of layers.

The hole transport layer acts to transport holes, which are injected from the anode, to the light emitting layer. The hole transport layer may be a monolayer or a stack of a plurality of layers.

The benzindolocarbazole derivatives represented by general formula (1-1) or (1-2) have an ionization potential of 5.1 to 6.0 eV (measurements from vapor-deposited film taken by AC-2 (Riken Keiki Co., Ltd.)), high triplet energy level, high hole transport efficiency, and thin film stability and therefore, they are used favorably as material of the hole injection layer and hole transport layer of a light emitting device. The structures represented by general formula (1-1) or (1-2) have a high triplet energy and therefore, they are used favorably as hole transport material for triplet light emitting material based devices. Conventional hole transport materials with a benzidine backbone are low in the triplet level and if in direct contact with a light emitting layer containing a triplet light emitting material, they will suffer a leak of triplet energy and deterioration in luminous efficiency. The benzindolocarbazole derivatives represented by general formula (1-1) or (1-2), however, will not suffer such a problem because they are high in triplet energy.

In the case of a device composed of a plurality of hole transport layers, the hole transport layer containing a benzindolocarbazole derivative as represented by general formula (1-1) or (1-2) is preferably in direct contact with the light emitting layer. This is because benzindolocarbazole derivatives as represented by general formula (1-1) or (1-2) are so high in electronic blocking capability that they can prevent the penetration of electrons flowing out of the light emitting layer. Furthermore, benzindolocarbazole derivatives as represented by general formula (1-1) or (1-2) are so high in triplet energy that they can effectively confine the excitation energy for triplet light emitting material. Accordingly, also in the case where triplet light emitting material is contained in the light emitting layer, the hole transport layer containing a benzindolocarbazole derivative represented by general formula (1-1) or (1-2) is preferably in direct contact with the light emitting layer.

The hole transport layer may be constituted only of a benzindolocarbazole derivative as represented by general formula (1-1) or (1-2) or may contain other materials as long as the advantageous effects of the invention are not impaired. Such other materials that can be used in this case include, for example, benzidine derivatives such as 4,4'-bis(N-(3-methylphenyl)-N-phenylamino) biphenyl (TPD), 4,4'-bis(N-(1-naphthyl)-N-phenylamino) biphenyl (NPD), 4,4'-bis(N,N-bis(4-biphenylyl) amino) biphenyl (TBDB), and bis(N,N'-diphenyl-4-aminophenyl)-N,N-diphenyl-4,4'-diamino-1,1'-biphenyl (TPD232); materials that are called starburst arylamines such as 4,4',4"-tris-(3-methylphenyl (phenyl)amino)triphenylamine (m-MTDATA), and 4,4',4"-tris-(1-naphthyl(phenyl)amino)triphenylamine (1-TNATA); biscarbazole derivatives such as bis(N-arylcarbazole) and bis(N-alkylcarbazole); heterocyclic compounds such as pyrazoline derivatives, stilbene based compounds, hydrazine based compounds, benzofuran derivatives, thiophene derivatives, oxadiazole derivatives, phthalocyanine derivatives, and porphyrin derivatives; and polymers such as polycarbonates and styrene derivatives containing any of the above-mentioned monomers in side chains as well as polythiophene, polyaniline, polyfluorene, polyvinyl carbazol, and polysilane.

The light emitting layer may be either a monolayer or a stack of a plurality of layers, and each layer contains a light emitting material (host material, dopant material), which may be a mixture of a host material and a dopant material, or a single host material, or a mixture of two host materials and one dopant material. This means that in the light emitting device according to the present invention, light emission in a light emitting layer may occur from either the host material or the dopant or may occur from both the host material and the dopant material. From the viewpoint of efficient use of electric energy for realizing light emission with high color purity, it is preferable for the light emitting layer to be formed of a mixture of a host material and a dopant material. The host material and the dopant material may be either a single material or a combination of a plurality of materials. The dopant material may exist either over the entirety of the host material or in a part thereof. The dopant material may be either laminated or dispersed. It is possible to control the luminescent color of the light from the dopant material. The dopant material can cause concentration quenching if its quantity is too large and therefore preferably accounts for 30 wt % or less, more preferably 20 wt % or less, of the host material. With respect to the doping method to be used, doping can be carried out by codeposition with the host material or by depositing a mixture with the host material prepared in advance.

It is possible to use a benzindolocarbazole derivative as represented by general formula (1-1) or (1-2) as a light emitting material and it is preferably used as host material in the light emitting layer particularly when a group as represented by general formula (7) is adopted as at least one of $Ar^1$ to $Ar^4$, which will work to increase the electronic affinity and enhance the electron injection efficiency.

In addition to the benzindolocarbazole derivatives represented by general formula (1-1) or (1-2), useful light emitting materials also include conventionally known light emitting materials such as anthracene, pyrene, and other fused ring derivatives; metal-chelated oxynoid compounds such as tris-(8-quinolinolato)aluminum; bisstyryl derivatives such as bisstyryl anthracene derivatives and distyryl benzene derivatives; and others such as tetraphenyl butadiene derivatives, indene derivatives, coumarin derivatives, oxadiazole derivatives, pyrrolopyridine derivatives, perinone derivatives, cyclopentadiene derivatives, oxadiazole derivatives, thiadiazolopyridine derivatives, dibenzofuran derivatives, carbazole derivatives, indolocarbazole derivatives, and polymer type ones such as polyphenylene vinylene derivatives, polyparaphenylene derivatives, and polythiophene derivatives, although the present invention is not limited thereto.

The host material contained in a light emitting material is not necessarily a single compound and it is possible to use a mixture of a plurality of the compounds according to the present invention, which may further contain one or more other host materials. Furthermore, they may be laminated. There are no specific limitations on the host materials and useful ones include compounds with a fused aryl ring such as naphthalene, anthracene, phenanthrene, pyrene, chrysene, naphthacene, triphenylene, perylene, fluoranthene, fluorene, and indene; derivatives thereof; aromatic amine derivatives such as n,n'-dinaphthyl-n,n'-diphenyl-4,4'-diphenyl-1,1'-diamine; metal-chelated oxynoid compounds such as tris-(8-quinolinato)aluminum (III); bisstyryl derivatives such as distyryl benzene derivatives; and others such as tetraphenyl butadiene derivatives, indene derivatives, coumarin derivatives, oxadiazole derivatives, pyrrolopyridine derivatives, perinone derivatives, cyclopentadiene derivatives, pyrrolopyrrole derivatives, thiadiazolopyridine derivatives, dibenzofuran derivatives, carbazole derivatives, indolocarbazole derivatives, triazine derivatives, and polymer type ones such as polyphenylene vinylene derivatives, polyparaphenylene derivatives, polyfluorene derivatives, polyvinyl carbazole derivatives, and polythiophene derivatives, although the present invention is not limited thereto. When the light emitting layer is designed for triplet light emission (phosphorescene emission), in particular, host materials that are preferred include metal-chelated oxynoid compounds, dibenzofuran derivatives, dibenzothiophene derivatives, carbazole derivatives, indolocarbazole derivatives, triazine derivatives, and triphenylene derivatives.

There are no specific limitations on the dopant materials contained in the light emitting material and examples include compounds with an aryl ring such as naphthalene, anthracene, phenanthrene, pyrene, triphenylene, perylene, fluorene, and indene; derivatives thereof such as 2-(benzothiazole-2-yl)-9,10-diphenyl anthracene and 5,6,11,12-tetraphenyl naphthacene; compounds with a heteroaryl ring such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, and thioxanthene; derivatives thereof; aminostyryl derivatives such as distyryl benzene derivatives, 4,4'-bis(2-(4-diphenylaminophenyl) ethenyl) biphenyl, and 4,4'-bis(N-(stilbene-4-yl)-N-phenylamino) stilbene; coumarin derivatives such as aromatic acetylene derivatives, tetraphenyl butadiene derivatives, stilbene derivatives, aldazine derivatives, pyrromethene derivatives, diketopyrro[3,4-c]pyrrole derivatives, and 2,3,5,6-1H,4H-tetrahydro-9-(2'-benzothiazolyl) quinolizino[9,9a,1-gh]coumarin; azole derivatives such as imidazole, thiazole, thiadiazole, carbazole, oxazole, oxadiazole, and triazole; metal complexes thereof; and aromatic amine derivatives such as N,N'-diphenyl-N,N'-di(3-methylphenyl)-4,4'-diphenyl-1,1'-diamine.

When the light emitting layer is designed for triplet light emission (phosphorescene emission), in particular, the dopant used is preferably a metal complex compound containing at least one metal selected from the group consisting of iridium (Ir), ruthenium (Ru), palladium (Pd), platinum (Pt), osmium (Os), and rhenium (Re). It is preferable for the ligand to contain a nitrogen-containing aromatic heterocyclic ring such as phenyl pyridine backbone, phenyl quinoline backbone, and carbine backbone. However, the dopant to be used is not limited thereto and an appropriate complex is selected based on the relations among the required luminescent color, device performance, and host compound. Specific examples include tris-(2-phenylpyridyl) iridium complex, tris-{2-(2-thiophenyl)pyridyl}iridium complex, tris-{2-(2-benzothiophenyl)pyridyl}iridium complex, tris-(2-phenylbenzothiazole) iridium complex, tris-(2-phenylbenzooxazole) iridium complex, tris-benzoquinoline iridium complex, bis(2-phenylpyridyl)(acetylacetonate) iridium complex, bis{2-(2-thiophenyl)pyridyl}iridium complex, bis{2-(2-benzothiophenyl)pyridyl}(acetylacetonate) iridium complex, bis(2-phenylbenzothiazole) (acetylacetonate) iridium complex, bis(2-phenylbenzooxazole) (acetylacetonate) iridium complex, bisbenzoquinoline (acetylacetonate) iridium complex, bis{2-(2,4-difluorophenyl) pyridyl}(acetylacetonate) iridium complex, tetraethylporphyrin platinum complex, {tris-(thenoyltrifluoroacetone)mono(1,10-phenanthroline)}europium complex, {tris-(thenoyltrifluoroacetone)mono(4,7-diphenyl-1,10-phenanthroline)}europium complex, {tris-(1,3-diphenyl-1,3-propanedione)mono(1,10-phenanthroline)}europium complex, and tris-acetylacetone terbium complex. In addition, phosphorescene dopants as described in Japanese Unexamined Patent Publication (Kokai) No. 2009-130141 are also used favorably. Being able to emit light with high efficiency, iridium complexes and platinum complexes are used favorably, although the present invention is not limited thereto.

The above-mentioned triplet light emitting materials used as dopant materials may be contained singly in the light emitting layer or used as a mixture of two or more thereof. If two or more triplet light emitting materials are used, the total weight of the dopant materials preferably accounts for 30 wt % or less, more preferably 20 wt % or less, of the host material.

In addition to the above host materials and triplet light emitting materials, the light emitting layer may further contain a third component with the aim of adjusting the carrier balance in the light emitting layer or stabilizing the layer structure of the light emitting layer. Such a third component, however, should be a material that does not interact with a host material containing a benzindolocarbazole derivative as represented by general formula (1-1) or (1-2) or with a dopant material containing a triplet light emitting material.

For triplet light emitting type layers, there are no specific limitations on the host and dopant to be used, but preferable ones include the following.

[Chemical formula 21]

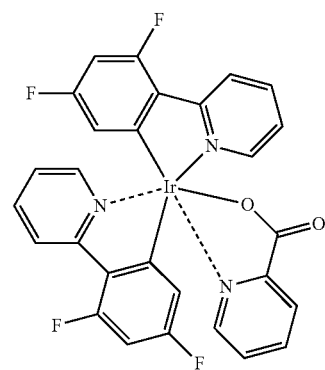

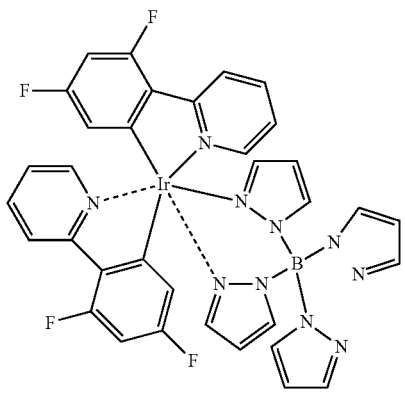

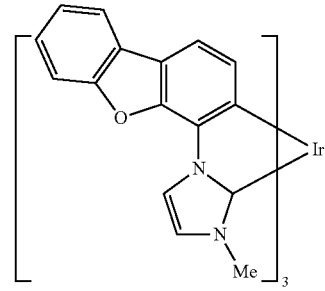

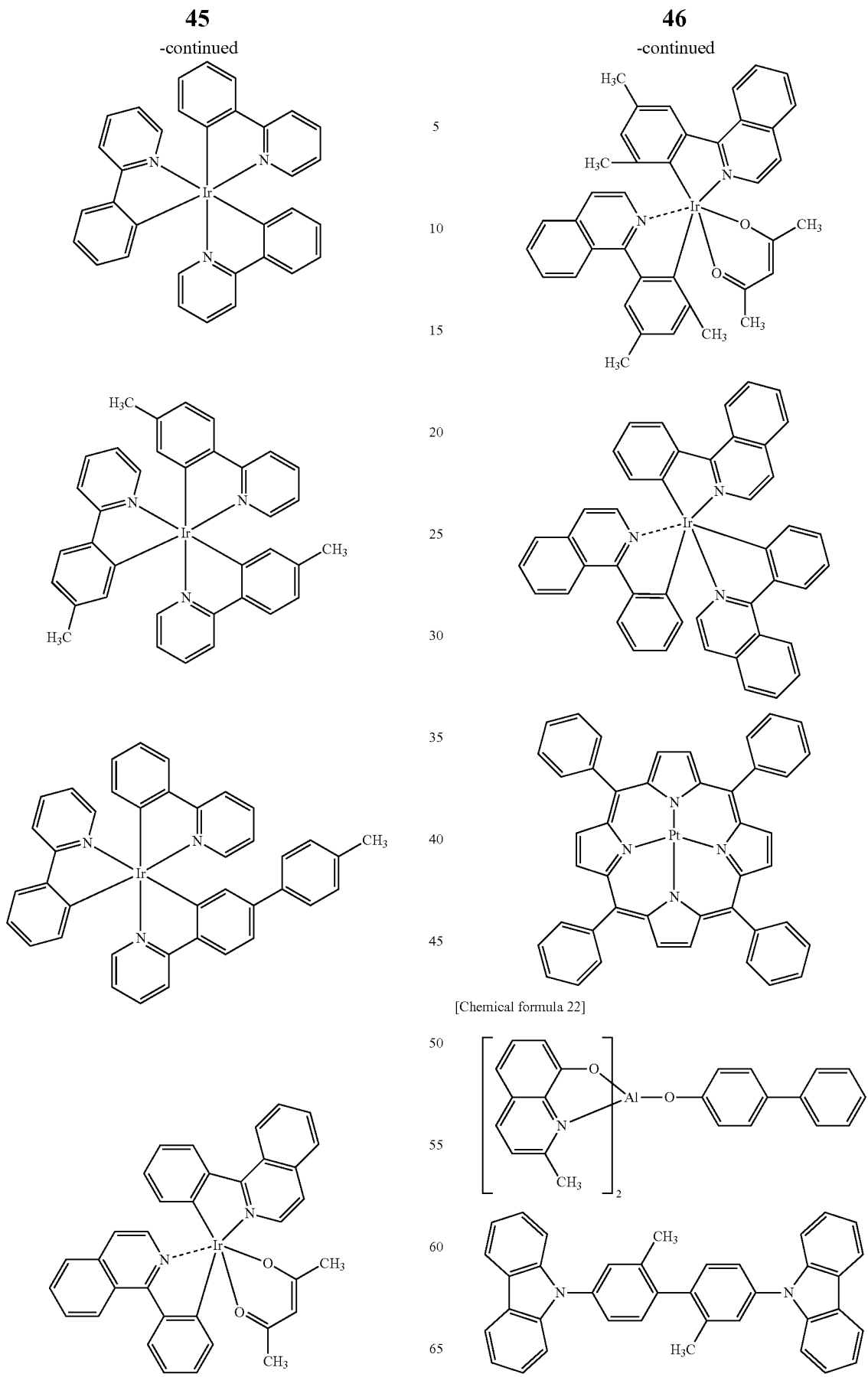
[Chemical formula 22]

-continued
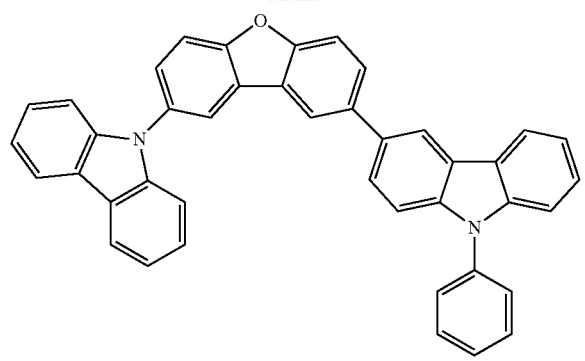
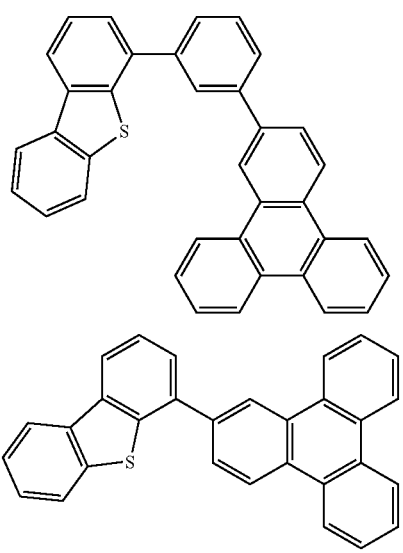
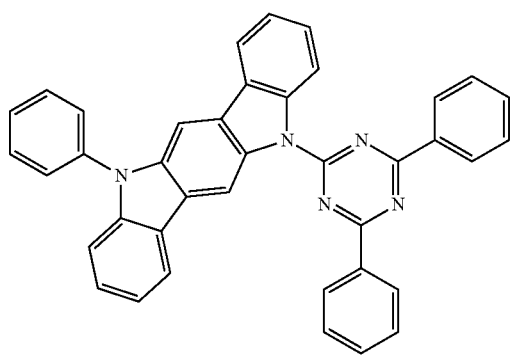
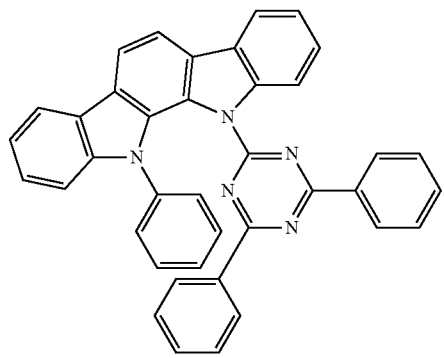
-continued
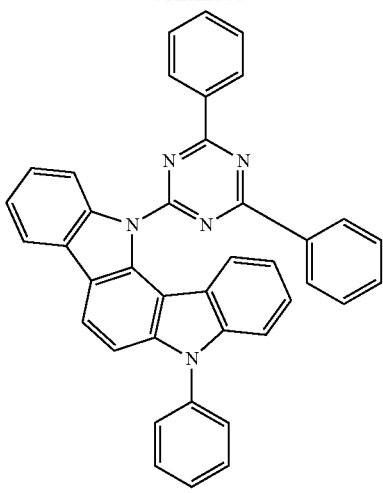
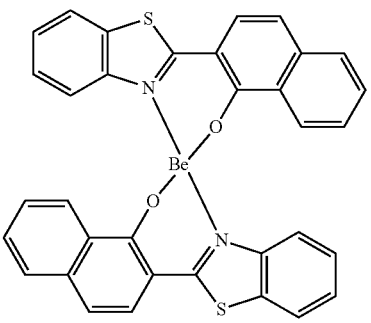
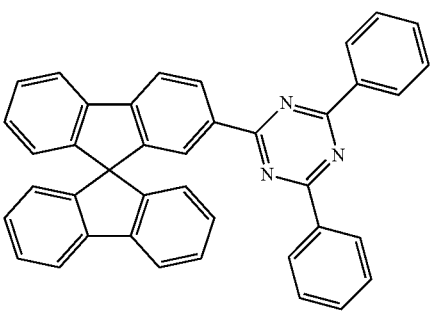
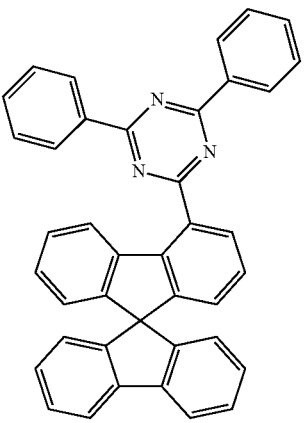

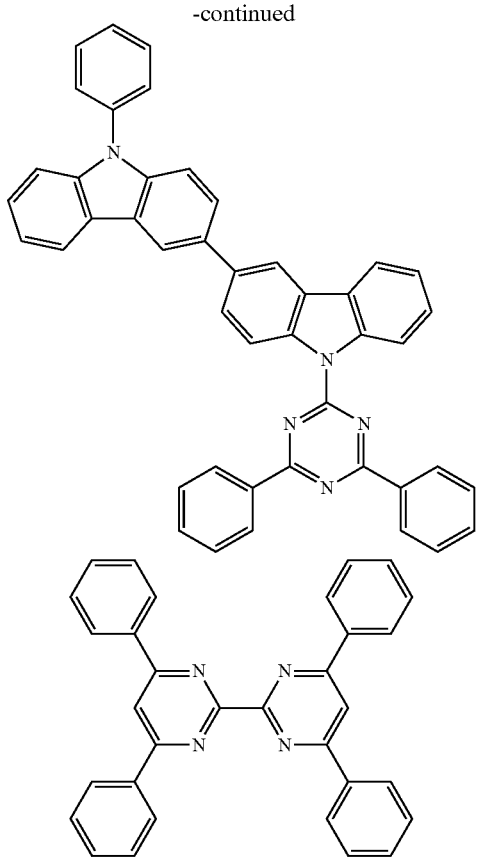

For the present invention, the electron transport layer is one that transport electrons injected from the cathode. The electron transport layer should be one that can ensure a high electron injection efficiency and transport the injected electrons efficiently. Accordingly, the electron transport layer should be of a material that is high in electron affinity, high in electron mobility, and also high in stability and does not suffer the generation of impurities that work as traps during production or use. If these layers are stacked to form a thick laminate, it is preferable to use compounds with a molecular weight of 400 or more because low molecular weight compounds tend to suffer quality degradation due to crystallization, leading to poor film quality. In view of the transport balance between holes and electrons, however, if the electron transport layer mainly plays the role of efficiently preventing the holes coming from the anode from flowing to the cathode without undergoing recombination, it can serve to improve the luminous efficiency as effectively as those formed of a material with high electron transport ability, even if it is formed of a material whose electron transport ability is not significantly high. Accordingly, a hole blocking layer that works efficiently to block the movement of the holes is regarded as the equivalent of the electron transport layer according to the present invention.

Electron transport materials that can be used to form an electron transport layer include fused polycyclic aromatic derivatives such as naphthalene and anthracene; styryl based aromatic ring derivatives such as 4,4'-bis(diphenylethenyl) biphenyl; quinone derivatives such as anthraquinone and diphenoquinone; quinolinol complexes such as phosphorus oxide derivatives and tris-(8-quinolinolate)aluminum (III); and various metal complexes such as benzoquinolinol complexes, hydroxyazole complexes, azo methine complexes, tropolone metal complexes, and flavonol metal complexes.

To ensure a reduced driving voltage and high luminous efficiency, it is preferable to use a compound having a heteroaryl ring structure that is formed of elements selected from the group consisting of carbon, hydrogen, nitrogen, oxygen, silicon, and phosphorus and contains an electron accepting nitrogen atom.

An electron accepting nitrogen atom as referred to herein is a nitrogen atom that is connected with an adjacent atom via a multiple bond. Such a nitrogen atom has a high electronegativity and accordingly, the multiple bond shows electron accepting properties. Thus, an aromatic heterocyclic ring containing an electron accepting nitrogen atom has a high electron affinity. An electron transport material containing electron accepting nitrogen atoms makes it easy to receive electrons from a cathode with a high electron affinity and facilitates driving at a low voltage. In addition, a larger number of electrons will be supplied to the light emitting layer and the recombination probability will increase, leading to an increase in the luminous efficiency.

Heteroaryl rings that contains an electron accepting nitrogen atom include, for example, pyridine ring, pyrazine ring, pyrimidine ring, quinoline ring, quinoxaline ring, naphthyridine ring, pyrimidopyrimidine ring, benzoquinoline ring, phenanthroline ring, imidazole ring, oxazole ring, oxadiazole ring, triazole ring, thiazole ring, thiadiazole ring, benzooxazole ring, benzothiazole ring, benzimidazole ring, and phenanthroimidazole ring.

Preferred compounds that has any of these heteroaryl ring structure include, for example, benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives (such as bipyridine and terpyridine), quinoxaline derivatives, and naphthyridine derivatives. From the viewpoint of electron transporting ability, particularly preferred ones include imidazole derivatives such as tris-(N-phenylbenzimidazole-2-yl)benzene, oxadiazole derivatives such as 1,3-bis[(4-tert-butyl phenyl) 1,3,4-oxadiazolyl]phenylene, triazole derivatives such as N-naphthyl-2,5-diphenyl-1,3,4-triazole, phenanthroline derivatives such as bathocuproine and 1,3-bis(1,10-phenanthroline-9-yl)benzene, benzoquinoline derivatives such as 2,2'-bis(benzo[h]quinoline-2-yl)-9,9'-spirobifluorene, bipyridine derivatives such as 2,5-bis(6'-(2',2"-bipyridyl))-1,1-dimethyl-3,4-diphenylsilole, terpyridine derivatives such as 1,3-bis(4'-(2,2':6'2"-terpyridinyl))benzene, and naphthyridine derivatives such as bis(1-naphthyl)-4-(1,8-naphthyridine-2-yl)phenylphosphine oxide. It is more preferable for these derivatives to have a fused polycyclic aromatic backbone because they will act to raise the glass transition temperature and increase the electron mobility, leading effectively to a low-voltage light emitting device. Furthermore, it is particularly preferable for the fused polycyclic aromatic backbone to be an anthracene backbone, pyrene backbone, or phenanthroline backbone because it serves to produce a device with a longer durable life, facilitate the synthesis process, and adopt widely available materials. The above electron transport materials may be used singly or a plurality of the electron transport materials may be used as a mixture. It may also be effective to use the above electron transport materials as a mixture with one or more other electron transport materials.

There are no specific limitations on the preferred electron transport materials, but specific examples include the following.

[Chemical formula 23]
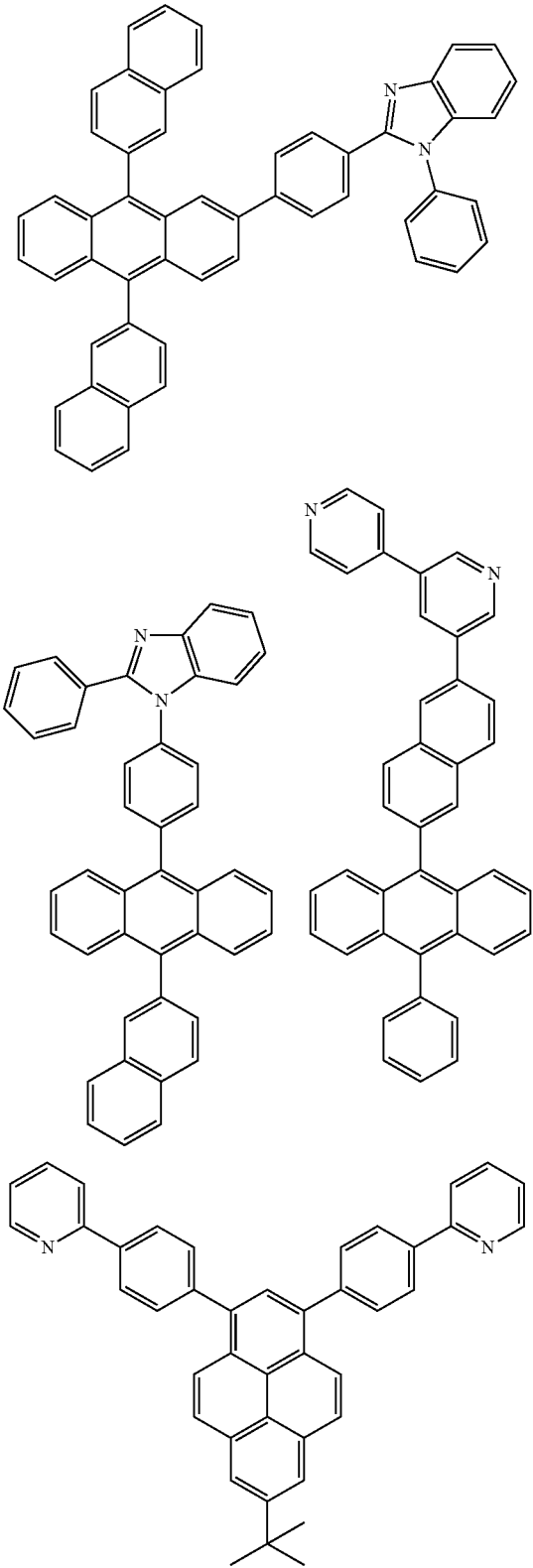
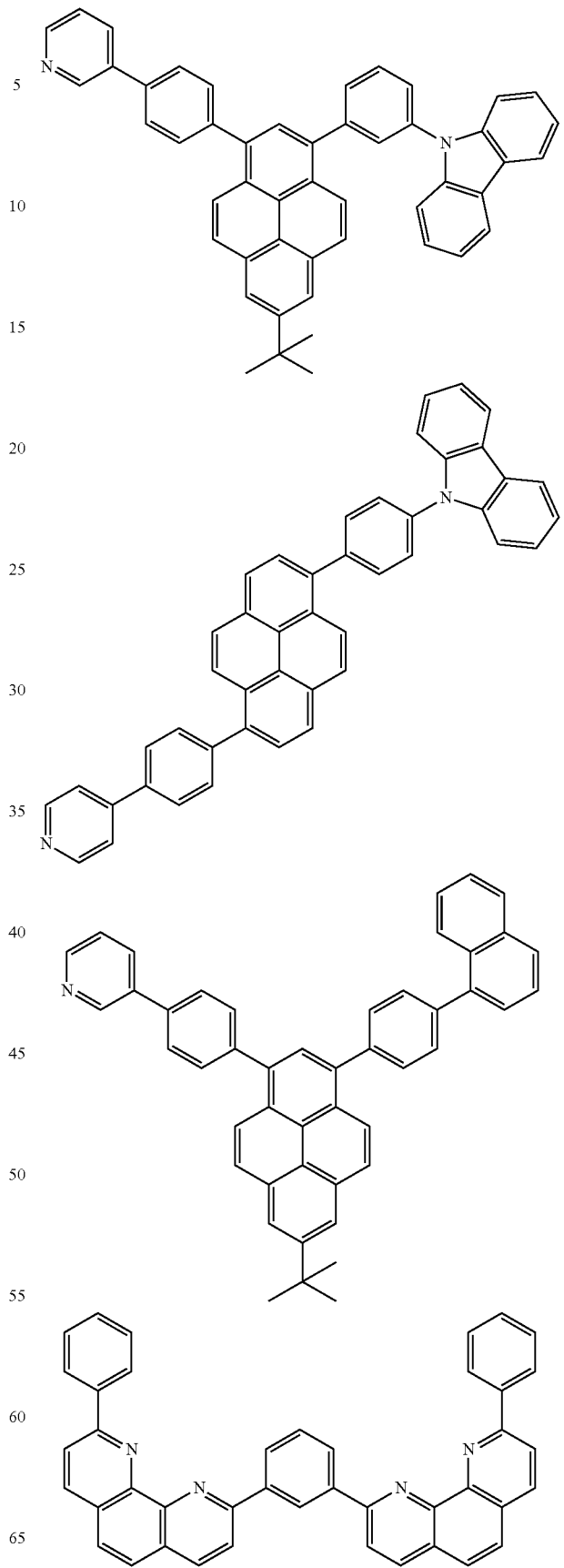

-continued

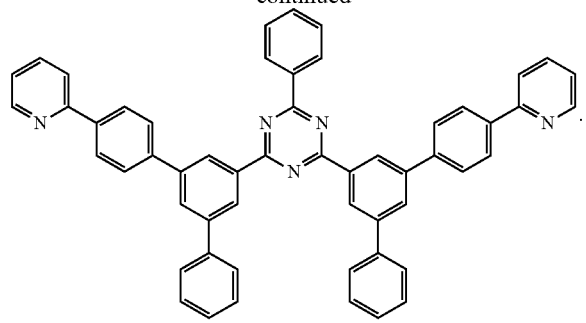

The above electron transport materials may be used singly or a plurality of the electron transport materials may be used as a mixture. It may also be effective to use the above electron transport materials as a mixture with one or more other electron transport materials. They may also contain a donor type compound. Here, a donor type compound is a compound that improves the electron injection barrier, thereby facilitating the electron injection from the cathode or electron injection layer to the electron transport layer, and increase the electric conductivity of the electron transport layer.

Preferable examples of such donor type compounds include alkali metals, inorganic salts containing an alkali metal, complexes of an alkali metal and an organic substance, alkaline earth metals, inorganic salts containing an alkaline earth metal, and complexes of an alkaline earth metal and an organic substance. Preferable alkali metals and alkaline earth metals include those having a low work function and serves effectively to realize an improved electron transporting capability. Such alkali metals include lithium, sodium, potassium, rubidium, and cesium, and such alkaline earth metals include magnesium, calcium, cerium, and barium.

Furthermore, using these metals in the form of an inorganic salt or a complex with an organic substance is more preferable than using them in the form of pure metal because of easy deposition and easy handling in a vacuum. Furthermore, it is more preferable for them to be in the form of a complex with an organic substance because of easy handling in atmosphere and easy control of their concentration. Examples of such inorganic salts include oxides such as LiO and $Li_2O$; nitrides; fluorides such as LiF, NaF, and KF; and carbonate such as $Li_2CO_3$, $Na_2CO_3$, $K_2CO_3$, $Rb_2CO_3$, $Cs_2CO_3$. Preferable examples of such alkali metals and alkaline earth metals include lithium and cesium, which serve effectively to allow low-voltage driving. Preferable examples of the organic substances used to form a complex with such an organic substance as above include quinolinol, benzoquinolinol, pyridyl phenol, flavonol, hydroxyimidazopyridine, hydroxybenzazole, and hydroxytriazole. In particular, the use of a complex of an alkali metal and an organic substance is preferable in view of its large effect in producing a low-voltage light emitting device, and the use of a complex of lithium and an organic substance is more preferable from the viewpoint of easy synthesis and high heat stability. Lithium quinolinol is particularly preferred because of its relatively low price.

There are no specific limitations on the ionization potential of the electron transport layer, but it is preferably 5.6 eV or more and 8.0 eV or less, more preferably 5.6 eV or more and 7.0 eV or less.

There are no specific limitations on the method for producing each of the layers that constitute the light emitting device and useful ones include resistance heating deposition, electron beam deposition, sputtering, molecule stacking, and coating, of which resistance heating deposition and electron beam deposition are commonly preferable from the viewpoint of device characteristics.

There are no specific limitations on the thickness of the organic layer because the optimum value depends on the resistance of the light emitting substance, but it is preferably in the range of 1 to 1,000 nm. The thickness of the light emitting layer, electron transport layer, and hole transport layer is preferably 1 nm or more and 200 nm or less, more preferably 5 nm or more and 100 nm or less.

The light emitting device according to the present invention has the function of converting electric energy to light. Here, as the electric energy, a direct current is commonly used, but it is also possible to use a pulse current or alternating current. There are no specific limitations on the electric current and voltage, but in view of the electric power consumption and device life, they should be such that a maximum brightness is realized at a low energy.

The light emitting device according to the present invention is used favorably, for example, as a component of a matrix and/or segment type display device.

A matrix type display contains pixels for display arranged in a two-dimensional pattern such as a grid and mosaic, and characters and images are displayed by groups of pixels. Appropriate pixel shape and size are adopted to meet the purpose of the display. For example, square pixels of 300 μm×300 μm or smaller are commonly used for character display in personal computers, monitoring devices, and TV screens, whereas large-size display devices such as display panels use pixels of millimeter-order size. Pixels of the same color are arranged in monochrome display devices, but red, green, and blue pixels are required for color displaying. For this purpose, delta type or stripe type devices are commonly used. With respect to the driving mechanism for the matrix, either the line sequential mechanism or the active matrix mechanism may be adopted. Line sequential driving systems have a simple structure, but active matrix driving systems are superior in terms of operating characteristics, so an appropriate one should be selected to meet particular purposes.

A segment type display device used for the present invention has a pattern designed to display intended information and light is emitted from the regions defined by the pattern. For example, devices of this type are used in digital clocks and thermometers for displaying time or temperature, audio equipment and electromagnetic cooking devices for displaying the operating state, and automobiles for panel displaying. Matrix displaying and segment displaying as described above can coexist in a panel.

The light emitting device according to the present invention can also be used favorably for backlight in various instruments. Backlight is intended mainly to improve the visibility of a display device that does not emit light by itself and incorporated in instruments such as liquid crystal display equipment, clocks, audio equipment, automobile panels, display boards, and signs. In particular, the light emitting device according to the present invention can be used favorably for backlight in liquid crystal display equipment, particularly for backlight in personal computers, for which active studies are now performed for developing thin displays, thus serving to provide backlight devices that are thin and lightweight compared to conventional ones.

EXAMPLES

The present invention will be illustrated below in greater detail with reference to examples, but it should be understood that the invention is not construed as being limited thereto. In the examples given below, the number accompanying each compound shows the corresponding one described above.

The minimum excited triplet energy of each compound was measured as follows. A compound was dissolved in 2-methyl tetrahydrofuran to prepare a solution of $1.0 \times 10^{-5}$ mol/l. The solution prepared was put in a special quartz tube and nitrogen bubbling was performed to remove dissolved oxygen, followed by capping the tube with a septum stopper to prevent the entry of oxygen. This sample was cooled to about 77K in liquid nitrogen and its phosphorescence spectrum was observed using a phosphorescence spectrophotometer (FluoroMax-4P, manufactured by Horiba, Ltd.). The wavelength at the position of build-up in the short wavelength region of the phosphorescene spectrum was measured and the triplet energy (T1) was calculated from the energy of light converted from the measured wavelength.

Synthesis Example 1

Synthesis of Compound [3]

A mixed solution of 35.09 g of α-tetralone, 21.69 g of phenylhydrazine hydrochloride, 9.0 g of acetic acid, and 500 ml of ethanol was heated while stirring for 7 hours under reflux in a flow of nitrogen. After cooling to room temperature, it was filtered and the filtrate was evaporated. The resulting solid was washed twice in 200 ml of purified water and vacuum-dried to provide 31.3 g of a light yellow solid. This solid was mixed with 38.6 g of chloranil and 377 ml of orthoxylene to prepare a solution, which was subjected to reflux for 1 hour in a flow of nitrogen. After cooling to room temperature, 300 ml of 10% aqueous sodium hydroxide solution was added, followed by stirring for 1 hour. The solution was filtered and the resulting solid was further washed 5 times with 200 ml of purified water. It was filtered and vacuum-dried to provide 18.97 g of 11H-benzo[a]carbazole (intermediate A). Then, a mixed solution of 18.0 g of intermediate A, 15.6 g of bromobenzene, 477 mg of bis(dibenzylidene acetone) palladium, 584 mg of di-t-butyl (2,2-diphenyl-1-methyl-1-cyclopropyl)phosphine, 11.15 g of sodium tert-butoxide, and 414 ml of o-xylene was heated while stirring for hours under reflux in a flow of nitrogen. After cooling to room temperature, extraction was performed with 300 ml of toluene. The organic layer was washed 3 times with 100 ml of water and dried with magnesium sulfate, followed by evaporation. The resulting condensate was purified by silica gel column chromatography and liquid was evaporated, followed by vacuum-drying the resulting solid to provide 17.0 g of 11-phenyl-11H-benzo[a]carbazole (intermediate B).

Then, a mixed solution of 17.0 g of intermediate B, 10.3 g of N-bromosuccinimido, and 290 ml of tetrahydrofuran was stirred for 3 hours at room temperature. After adding 300 ml of water, it was filtered and vacuum-drying was performed to provide 21.47 g of 5-bromo-11-phenyl-11H-benzo[a]carbazole (intermediate C).

Subsequently, a mixed solution of 26.0 g of intermediate C, 26.6 g of bis(pinacolato)diboron, 1.14 g of 1,1'-bis(diphenylphosphino)ferrocene dichloropalladium (II), 2.1 g of potassium acetate, and 350 ml of dimethyl formamide was heated while stirring at 135° C. for 2.5 hours in a flow of nitrogen. After cooling to room temperature, 300 ml of purified water and 300 ml of ethyl acetate were added, followed by celite filtration. The organic layer was recovered from the filtrate and dried with magnesium sulfate, followed by filtration and evaporation. The resulting condensate was purified by silica gel column chromatography and liquid was evaporated, followed by vacuum-drying the resulting solid to provide 17.46 g of 11-phenyl-5-(4,4,5,5,-tetramethyl-1,3,2-dioxaborolan-2-yl) 11H-benzo[a]carbazole (intermediate D).

Then, a mixed solution of 17.46 g of intermediate D, 9.43 g of 2-iodonitrobenzene, 531 mg of dichlorobis(triphenylphosphine) palladium (II), 56 ml of 1.5 M aqueous sodium carbonate solution, and 208 ml of dimethoxy ethane was subjected to reflux in a flow of nitrogen for 1 hour. After cooling to room temperature, 200 ml of purified water was added and the solution was filtered. The solid resulting from vacuum drying was purified by silica gel column chromatography and liquid was evaporated, followed by vacuum-drying the resulting solid to provide 11.27 g of 5-(2-nitrophenyl)-11-phenyl-11H-benzo[a]carbazole (intermediate E).

Then, a mixed solution of 11.27 g of intermediate E, 17.79 g of triphenylphosphine, and 54 ml of orthodichlorobenzene was heated while stirring for 8 hours under reflux in a flow of nitrogen. After cooling to room temperature, liquid was evaporated from the mixed solution. The resulting condensate was purified by silica gel column chromatography and liquid was evaporated, followed by vacuum-drying the resulting solid to provide 9.66 g of 5-phenyl-5,14-dihydrobenzo[a]indolo[3,2-c]carbazole (intermediate F).

Then, a mixed solution of 2.0 g of intermediate F, 1.86 g of 3-bromotriphenylamine, 60 mg of bis(dibenzylidene acetone) palladium, 74 mg of di-t-butyl (2,2-diphenyl-1-methyl-1-cyclopropyl)phosphine, 604 mg of sodium tert-butoxide, and 26 ml of orthoxylene was heated while stirring for 3 hours under reflux in a flow of nitrogen. After cooling to room temperature, 26 ml of purified water was added and the solution was subjected to celite filtration. The organic layer was dried with magnesium sulfate, followed by filtration and evaporation. The resulting condensate was purified by silica gel column chromatography and liquid was evaporated, followed by vacuum-drying the resulting solid to provide 2.18 g of compound [3].

The resulting powder was subjected to $^1$H-NMR analysis and the following results were obtained, showing that the white solid obtained above was compound [3].

$^1$H-NMR (CDCL$_3$ (d=ppm)): 6.61-6.64 (d, 1H, J=8.1), 6.90-7.70 (m, 28H), 8.60-8.63 (m, 1H), 8.96-8.99 (d, 1H, J=8.37).

Compound [3] obtained here was used as material to produce a light emitting device after being purified by sublimation at about 330° C. under a pressure of $1 \times 10^{-3}$ Pausing an oil diffusion pump. The HPLC purity (area % at measuring wavelength of 254 nm) was 99.9% before purification by sublimation and 99.9% after purification by sublimation. In addition, the minimum excited triplet energy level T1 of compound [3] was 2.51 eV.

Synthesis Example 2

Synthesis of Compound [12]

Then, a mixed solution of 2.5 g of intermediate F, 1.91 g of 5'-chloro-5'-chloro-1,1':3',1''-terphenyl, 75 mg of bis(dibenzylidene acetone) palladium, 92 mg of di-t-butyl (2,2-diphenyl-1-methyl-1-cyclopropyl)phosphine, 754 mg of sodium tert-butoxide, and 33 ml of orthoxylene was heated while stirring for 1 hour under reflux in a flow of nitrogen. After cooling to room temperature, 33 ml of purified water was added and the solution was subjected to celite filtration. The organic layer was dried with magnesium sulfate, followed by filtration and evaporation. The resulting condensate was purified by silica gel column chromatography and liquid was evaporated, followed by vacuum-drying the resulting solid to provide 3.67 g of compound 12.

The resulting powder was subjected to $^1$H-NMR analysis and the following results were obtained, showing that the white solid obtained above was compound [2].

$^1$H-NMR (CDCL$_3$ (d=ppm)): 6.31-6.34 (d, 1H, J=8.10), 6.75-6.80 (t, 1H), 7.04-7.72 (m, 23H), 7.88-7.89 (m, 2H), 8.08 (s, 1H), 8.68-8.71 (d, 1H, J=7.83), 9.05-9.08 (d, 1H, J=8.10).

Compound [12] obtained here was used as material to produce a light emitting device after being purified by sublimation at about 330° C. under a pressure of 1×10$^{-3}$ Pa using an oil diffusion pump. The HPLC purity (area % at measuring wavelength of 254 nm) was 99.9% before purification by sublimation and 99.9% after purification by sublimation. In addition, the minimum excited triplet energy level T1 of compound [12] was 2.51 eV.

Example 1

From a glass substrate carrying a deposited transparent electrically conductive film of ITO with a thickness of 50 nm (manufactured by Geomatec Co., Ltd., 11 Ω/□, sputtered product), a 38×46 mm piece was cut out and etched. The resulting substrate was subjected to ultrasonic cleaning for 15 minutes with Semico Clean 56 (trade name, manufactured by Furuuchi Chemical Corporation) and then washed with ultrapure water. Immediately before device production, this substrate was subjected to UV ozone treatment for 1 hour and placed in vacuum evaporation equipment, which was then exhausted to a vacuum of below 5×10$^{-4}$ Pa. It was subjected to resistance heating to deposit 10 nm of compound HI-1 to form a hole injection layer. Then, 80 nm of compound HT-1 was deposited to form a first hole transport layer. Then, 40 nm of compound [1] was deposited to form a second hole transport layer. Subsequently, compound H-1 used as host material and compound D-1 used as dopant material were deposited in such a manner that the doping concentration of the dopant material is 10 wt % to form a light emitting layer with a thickness of 30 nm. Then, 35 nm of compound E-1 was formed on top of it as an electron transport layer.

Subsequently, lithium quinolinol was deposited to a thickness of 1 nm and then magnesium and silver were codeposited at a deposition rate ratio between magnesium and silver of 10:1 (=0.5 nm/s:0.05 nm/s) to form a cathode with a thickness of 100 nm, thus providing a device of a 5×5 mm square. The film thickness referred to above was the reading on a crystal oscillation type film thickness monitor. When this light emitting device was driven by a direct current of 10 mA/cm$^2$, highly efficient red light emission was realized with a luminous efficiency of 13.9 lm/W. When this light emitting device was driven by a direct current of 10 mA/cm$^2$, the brightness was reduced to 50% in 3,950 hours. Here, compounds HI-1, HT-6, H-1, D-1, and E-1 are as shown below.

[Chemical formula 24]

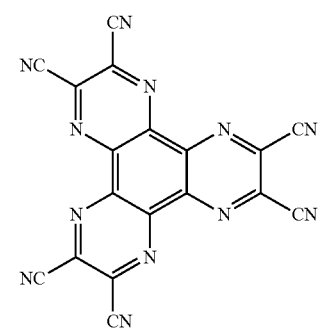
HI-1

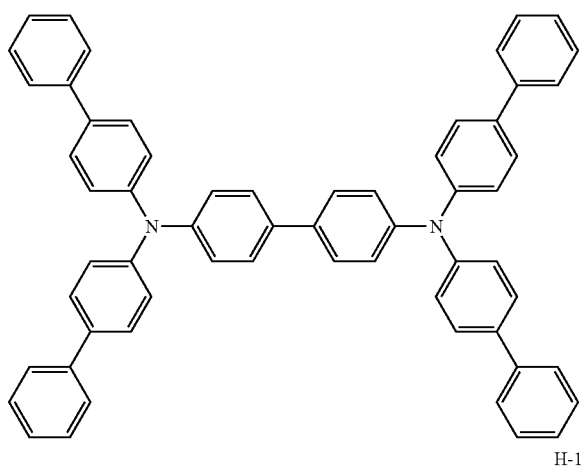
HT-1

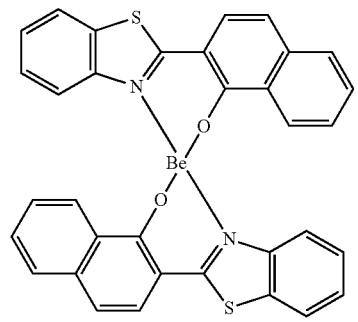
H-1

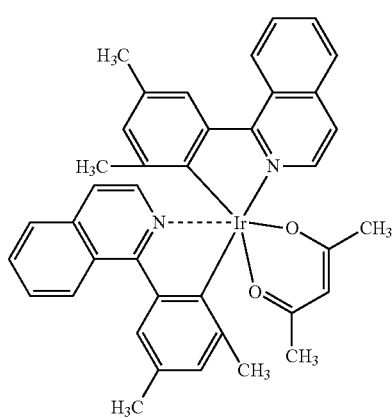
D-1

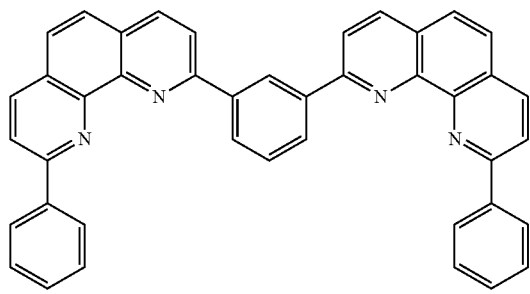

E-1

Examples 2 to 8 and Comparative Examples 1 to 5

Except that a material as given in Table 1 was used for the second hole transport layer, the same procedure as in Example 1 was carried out to produce a light emitting device. Results are given in Table 1. Here, compounds HT-2, HT-3, HT-4, and HT-5 are as shown below.

[Chemical formula 25]

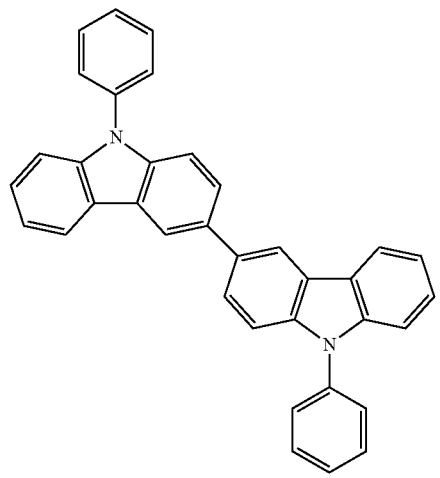

HT-2

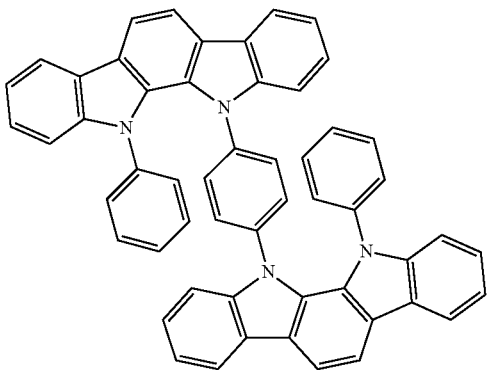

HT-3

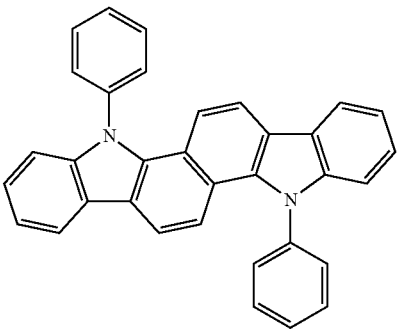

HT-4

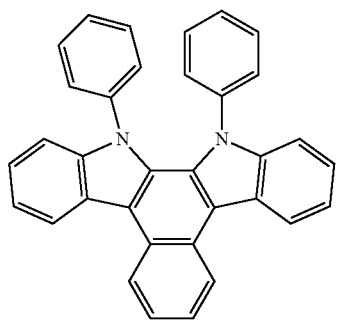

HT-5

[Table 1]

TABLE 1

| | Hole injection layer | First hole transport layer | Second hole transport layer | Host material | Dopant material | Electron transport layer | Emission color | Light emitting efficiency (lm/W) | Brightness half-life (h) |
|---|---|---|---|---|---|---|---|---|---|
| Example 1 | HI-1 | HT-1 | compound [1] | H-1 | D-1 | E-1 | red | 13.7 | 3950 |
| Example 2 | | | compound [12] | | | | | 13.3 | 3800 |
| Example 3 | | | compound [16] | | | | | 13.6 | 3850 |
| Example 4 | | | compound [17] | | | | | 13.4 | 3900 |
| Example 5 | | | compound [19] | | | | | 13.6 | 3900 |
| Example 6 | | | compound [27] | | | | | 13.9 | 3950 |
| Example 7 | | | compound [29] | | | | | 14.0 | 4100 |
| Example 8 | | | compound [31] | | | | | 13.8 | 4000 |
| Comparative example 1 | HI-1 | HT-1 | HT-1 | H-1 | D-1 | E-1 | red | 7.0 | 1000 |
| Comparative example 2 | | | HT-2 | | | | | 10.5 | 1100 |
| Comparative example 3 | | | HT-3 | | | | | 9.0 | 900 |
| Comparative example 4 | | | HT-4 | | | | | 10.5 | 1200 |
| Comparative example 5 | | | HT-5 | | | | | 11.0 | 1500 |

Example 9

From a glass substrate carrying a deposited transparent electrically conductive film of ITO with a thickness of 50 nm (manufactured by Geomatec Co., Ltd., 11 Ω/□, sputtered product), a 38×46 mm piece was cut out and etched. The resulting substrate was subjected to ultrasonic cleaning for 15 minutes with Semico Clean 56 (trade name, manufactured by Furuuchi Chemical Corporation) and then washed with ultrapure water. Immediately before device production, this substrate was subjected to UV ozone treatment for 1 hour and placed in vacuum evaporation equipment, which was then exhausted to a vacuum of below $5\times10^{-4}$ Pa. It was subjected to resistance heating to deposit 10 nm of compound HI-1 to form a first hole injection layer. Then, 10 nm of compound [1] was deposited to form a second hole injection layer. Then, 80 nm of HT-1 was deposited to form a hole transport layer. Subsequently, compound H-1 used as host material and compound D-1 used as dopant material were deposited in such a manner that the doping concentration of the dopant material is 10 wt % to form a light emitting layer with a thickness of 30 nm. Then, 35 nm of compound E-1 was formed on top of it as an electron transport layer.

Then, lithium fluoride was deposited to 0.5 nm and aluminum was deposited to 1,000 nm to form a cathode, thereby providing a device of a 5×5 mm square. The film thickness referred to above was the reading on a crystal oscillation type film thickness monitor. When this light emitting device was driven by a direct current 10 mA/cm$^2$, highly efficient red light emission was realized with a luminous efficiency of 8.7 lm/W. When this light emitting device was driven by a direct current of 10 mA/cm$^2$, the brightness was reduced to 50% in 1,900 hours.

Examples 10 to 16 and Comparative Examples 6 to 10

Except that a material as given in Table 2 was used for the second hole injection layer, the same procedure as in Example 9 was carried out to produce a light emitting device. Results are given in Table 2.

Example 17

From a glass substrate carrying a deposited transparent electrically conductive film of ITO with a thickness of 50 nm (manufactured by Geomatec Co., Ltd., 11 Ω/□, sputtered product), a 38×46 mm piece was cut out and etched. The resulting substrate was subjected to ultrasonic cleaning for 15 minutes with Semico Clean 56 (trade name, manufactured by Furuuchi Chemical Corporation) and then washed with ultrapure water. Immediately before device production, this substrate was subjected to UV ozone treatment for 1 hour and placed in vacuum evaporation equipment, which was then exhausted to a vacuum of below $5\times10^{-4}$ Pa. It was subjected to resistance heating to deposit 10 nm of HI-1 to form a hole injection layer. Then, 90 nm of compound HT-1 was deposited to form a hole transport layer. Subsequently, compound [21] used as host material and compound D-1 used as dopant material were deposited in such a manner that the doping concentration of the dopant material is 10 wt % to form a light emitting layer with a thickness of 30 nm. Then, 35 nm of compound E-1 was formed on top of it as an electron transport layer.

Then, lithium fluoride was deposited to 0.5 nm and aluminum was deposited to 1,000 nm to form a cathode, thereby providing a device of a 5×5 mm square. The film thickness referred to above was the reading on a crystal oscillation type film thickness monitor. When this light emitting device was driven by a direct current 10 mA/cm$^2$, highly efficient red light emission was realized with a luminous efficiency of 11.9 hi/W. When this light emitting device was driven by a direct current of 10 mA/cm$^2$, the brightness was reduced to 50% in 2,900 hours.

Examples 18 to 20 and Comparative Example 11

Except that a material as given in Table 3 was used as host material for the light emitting layer, the same procedure as in Example 17 was carried out to produce a light emitting device, which was then evaluated. Results are given in Table 3.

TABLE 2

| | First hole injection layer | Second hole injection layer | Hole transport layer | Host material | Dopant material | Electron transport layer | Emission color | Luminous efficiency (lm/w) | Brightness half-life (h) |
|---|---|---|---|---|---|---|---|---|---|
| Example 9 | HI-1 | compound [1] | HT-1 | H-1 | D-1 | E-1 | red | 8.7 | 1900 |
| Example 10 | | compound [12] | | | | | | 8.3 | 1950 |
| Example 11 | | compound [16] | | | | | | 8.8 | 1900 |
| Example 12 | | compound [17] | | | | | | 8.5 | 1850 |
| Example 13 | | compound [19] | | | | | | 8.5 | 1900 |
| Example 14 | | compound [27] | | | | | | 9.2 | 1950 |
| Example 15 | | compound [29] | | | | | | 9.4 | 2100 |
| Example 16 | | compound [31] | | | | | | 9.3 | 2050 |
| Comparative example 6 | HI-1 | HT-1 | HT-1 | H-1 | D-1 | E-1 | red | 7.0 | 1000 |
| Comparative example 7 | | HT-2 | | | | | | 5.0 | 500 |
| Comparative example 8 | | HT-3 | | | | | | 4.0 | 300 |
| Comparative example 9 | | HT-4 | | | | | | 7.5 | 800 |
| Comparative example 10 | | HT-5 | | | | | | 7.5 | 900 |

TABLE 3

| | Hole injection layer | Hole transport layer | Host material | Dopant material | Electron transport layer | Emission color | Luminous efficiency (lm/W) | Brightness half-life (h) |
|---|---|---|---|---|---|---|---|---|
| Example 17 | HI-1 | HT-1 | compound [21] | D-1 | E-1 | red | 11.9 | 2900 |
| Example 18 | | | compound [23] | | | | 11.8 | 2800 |
| Example 19 | | | compound [36] | | | | 12.3 | 3000 |
| Example 20 | | | compound [46] | | | | 12.5 | 2950 |
| Comparative example 11 | HI-1 | HT-1 | H-1 | D-1 | E-1 | red | 7.0 | 1000 |

Example 21

From a glass substrate carrying a deposited transparent electrically conductive film of ITO with a thickness of 165 nm (manufactured by Geomatec Co., Ltd., 11 Ω/□, sputtered product), a 38×46 mm piece was cut out and etched. The resulting substrate was subjected to ultrasonic cleaning for 15 minutes with Semico Clean 56 (trade name, manufactured by Furuuchi Chemical Corporation) and then washed with ultrapure water. Immediately before device production, this substrate was subjected to UV ozone treatment for 1 hour and placed in vacuum evaporation equipment, which was then exhausted to a vacuum of below 5×10$^{-4}$ Pa. Resistance heating was performed to deposit HI-1 first to 5 nm to form a hole injection layer and deposit compound [1] to 80 nm to form a hole transport layer. Subsequently, host material H-2 and dopant material D-2 were deposited in such a manner that the doping concentration of the dopant material is 5 wt % to form a light emitting layer with a thickness of 40 nm. Then, a 30 nm layer of E-1 was deposited on top of it as an electron transport layer. Then, lithium fluoride was deposited to 0.5 nm and aluminum was deposited to 1,000 nm to form a cathode, thereby providing a device of a 5×5 mm square. The film thickness referred to above was the reading on a crystal oscillation type film thickness monitor. This light emitting device was subjected to characteristics examination at 1,000 cd/m$^2$ and found to have an external quantum efficiency of 4.4%. When this light emitting device was driven by a direct current of 10 mA/cm$^2$, the brightness was reduced to 50% in 1,050 hours. Here, H-2 and D-2 are compounds as shown below.

[Chemical formula 26]

H-2

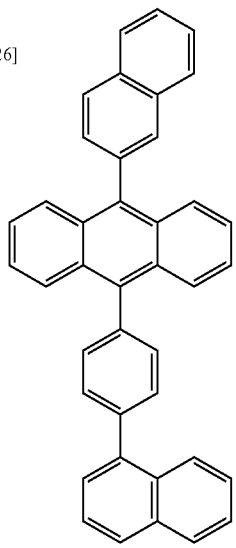

D-2

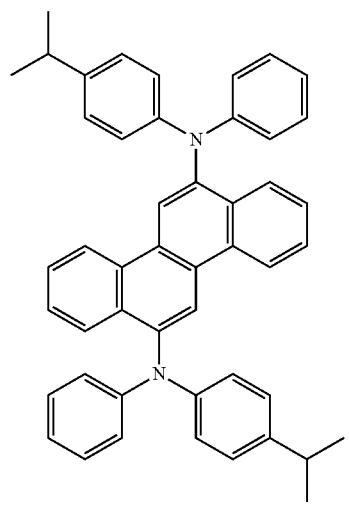

Examples 22 to 28 and Comparative Examples 12 to 16

Except that a material as given in Table 4 was used for the hole transport layer, the same procedure as in Example 21 was carried out to produce a light emitting device. Results are given in Table 4.

TABLE 4

| | Hole injection layer | Hole transport layer | Host material | Dopant material | Electron transport layer | Emission color | External quantum efficiency (%) | Brightness half-life (h) |
|---|---|---|---|---|---|---|---|---|
| Example 21 | HI-1 | compound [1] | H-2 | D-2 | E-1 | blue | 4.4 | 1050 |
| Example 22 | | compound [12] | | | | | 4.3 | 1050 |
| Example 23 | | compound [16] | | | | | 4.2 | 900 |
| Example 24 | | compound [17] | | | | | 4.4 | 950 |
| Example 25 | | compound [19] | | | | | 4.5 | 1000 |
| Example 26 | | compound [27] | | | | | 4.8 | 1100 |
| Example 27 | | compound [29] | | | | | 4.9 | 1150 |
| Example 28 | | compound [31] | | | | | 4.7 | 1100 |
| Comparative example 12 | HI-1 | HT-1 | H-2 | D-2 | E-1 | blue | 2.7 | 300 |
| Comparative example 13 | | HT-2 | | | | | 3.5 | 350 |
| Comparative example 14 | | HT-3 | | | | | 3.3 | 400 |
| Comparative example 15 | | HT-4 | | | | | 3.0 | 500 |
| Comparative example 16 | | HT-5 | | | | | 3.8 | 550 |

The invention claimed is:

1. A benzindolocarbazole derivative as represented by either general formula (1-1) or (1-2) given below:

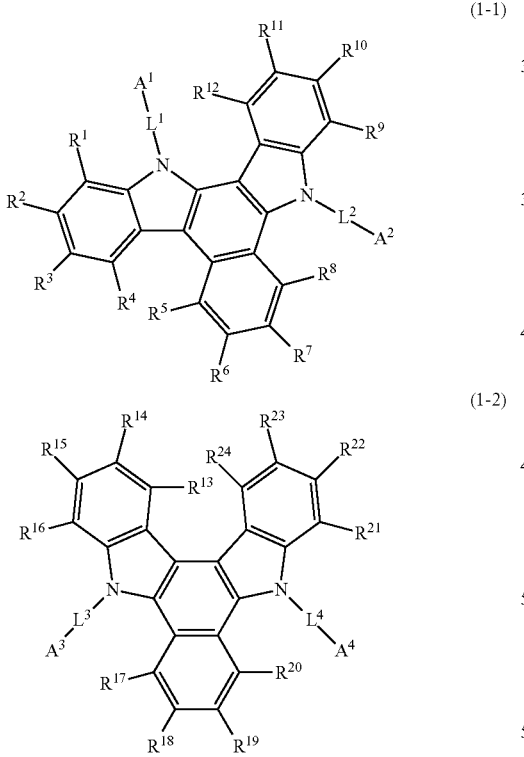

wherein $R^1$ to $R^{24}$ may be identical to or different from each other and are selected from the group consisting of a hydrogen atom, alkyl group, cycloalkyl group, heterocyclic group, amino group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group, carbamoyl group, silyl group, and —P(=O)$R^{25}R^{26}$; $R^{25}$ and $R^{26}$ represent an aryl group or a heteroaryl group; $R^{25}$ and $R^{26}$ may be condensed to form a ring; $L^1$ to $L^4$ independently represent a single bond, a substituted or unsubstituted arylene group, or a substituted or unsubstituted heteroarylene group; and $A^1$ to $A^4$ independently represent an amino group, aryl group, heterocyclic group, or heteroaryl group.

2. A benzindolocarbazole derivative as described in claim 1, wherein at least either $A^1$ or $A^2$ in general formula (1-1) or at least either $A^3$ or $A^4$ in general formula (1-2) is a group as represented by any of general formulae (2) to (7) given below:

wherein $R^{27}$ and $R^{28}$ may be identical to or different from each other and are selected from the group consisting of an aryl group, heteroaryl group, polycyclic aromatic hydrocarbon group, and polycyclic aromatic heterocyclic group; and the derivative is connected to either $L^1$ or $L^2$ in general formula (1-1) given above or either $L^3$ or $L^4$ in general formula (1-2) given above at the position indicated by *;

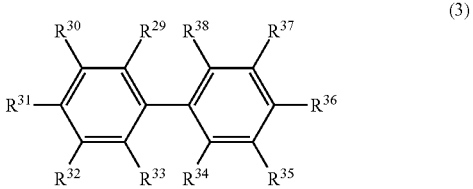

wherein, $R^{29}$ to $R^{38}$ may be identical to or different from each other and are selected from the group consisting of a hydrogen atom, alkyl group, cycloalkyl group, aryl group, heterocyclic group, alkenyl group, cycloalkenyl group, alkynyl group, halogen atom, carbonyl group, carboxyl group, oxycarbonyl group, carbamoyl group, silyl group, and —P(=O)$R^{39}R^{40}$; $R^{39}$ and $R^{40}$ represent an aryl group or a heteroaryl group; $R^{39}$ and $R^{40}$ may be condensed to form a ring; and the derivative is connected to either $L^1$ or $L^2$ in general formula (1-1) given above or either $L^3$ or $L^4$ in general formula (1-2) given above at the position of any of $R^{29}$ to $R^{38}$;

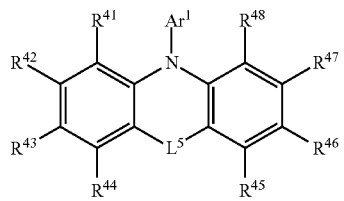

(4)

wherein, $R^{41}$ to $R^{48}$ may be identical to or different from each other and are selected from the group consisting of a hydrogen atom, alkyl group, cycloalkyl group, heterocyclic ring, amino group, alkenyl group, cycloalkenyl group, alkynyl group, halogen atom, carbonyl group, carboxyl group, oxycarbonyl group, carbamoyl group, silyl group, and —P(=O)$R^{49}R^{50}$; $R^{49}$ and $R^{50}$ represent either an aryl group or a heteroaryl group; $R^{49}$ and $R^{50}$ may be condensed to form a ring; $Ar^1$ denotes a substituted or unsubstituted aryl group or a substituted or unsubstituted heteroaryl group; $L^5$ denotes $CH_2$, N—$Ar^2$, an oxygen atom, or sulfur atom; when $L^5$ is $CH_2$, at least either of the hydrogen atoms may be replaced with an alkyl group; $Ar^2$ denotes a substituted or unsubstituted aryl group or a substituted or unsubstituted heteroaryl group; and the derivative is connected to either $L^1$ or $L^2$ in general formula (1-1) given above or either $L^3$ or $L^4$ in general formula (1-2) given above at the position of either any of $R^{41}$ to $R^{48}$ or $Ar^1$;

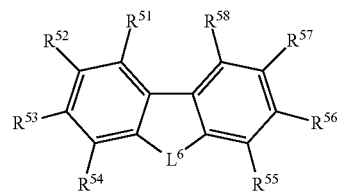

(5)

wherein $R^{51}$ to $R^{58}$ may be identical to or different from each other and are selected from the group consisting of a hydrogen atom, alkyl group, cycloalkyl group, aryl group, heterocyclic group, alkenyl group, cycloalkenyl group, alkynyl group, halogen atom, carbonyl group, carboxyl group, oxycarbonyl group, carbamoyl group, silyl group, and —P(=O)$R^{59}R^{60}$; $R^{59}$ and $R^{60}$ represent either an aryl group or a heteroaryl group; $R^{59}$ and $R^{60}$ may be condensed to form a ring; $L^6$ denotes $CH_2$, N—$Ar^3$, an oxygen atom, or sulfur atom; $Ar^3$ denotes a substituted or unsubstituted aryl group or a substituted or unsubstituted heteroaryl group; when $L^6$ is $CH_2$, at least either of the hydrogen atoms may be replaced with an alkyl group; and the derivative is connected to either $L^1$ or $L^2$ in general formula (1-1) given above or either $L^3$ or $L^4$ in general formula (1-2) given above at the position of any of $R^{51}$ to $R^{58}$;

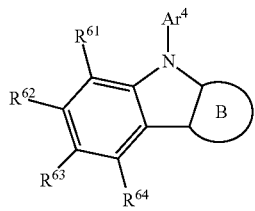

(6)

wherein ring B represents a substituted or unsubstituted condensed aromatic hydrocarbon ring, substituted or unsubstituted monocyclic aromatic heterocyclic ring, or substituted or unsubstituted condensed aromatic heterocyclic ring; $R^{61}$ to $R^{64}$ may be identical to or different from each other and are selected from the group consisting of a hydrogen atom, alkyl group, cycloalkyl group, heterocyclic group, alkenyl group, cycloalkenyl group, alkynyl group, alkoxy group, alkylthio group, aryl ether group, aryl thioether group, aryl group, heteroaryl group, halogen atom, carbonyl group, carboxyl group, oxycarbonyl group and carbamoyl group, silyl group, and —P(=O)$R^{65}R^{66}$; $R^{65}$ and $R^{66}$ represent either an aryl group or a heteroaryl group; $R^{65}$ and $R^{66}$ may be condensed to form a ring; $Ar^4$ denotes a substituted or unsubstituted aryl group or a substituted or unsubstituted heteroaryl group; and the derivative is connected to either $L^1$ or $L^2$ in general formula (1-1) given above or either $L^3$ or $L^4$ in general formula (1-2) given above at the position of any of $R^{61}$ to $R^{64}$, $Ar^4$, and ring B;

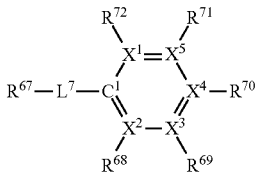

(7)

wherein $R^{67}$ to $R^{72}$ may be identical to or different from each other and are selected from the group consisting of a hydrogen atom, alkyl group, cycloalkyl group, aryl group, heterocyclic group, alkenyl group, cycloalkenyl group, alkynyl group, halogen atom, carbonyl group, carboxyl group, oxycarbonyl group, carbamoyl group, silyl group, and —P(=O)$R^{73}R^{74}$; $R^{73}$ and $R^{74}$ represent either an aryl group or a heteroaryl group; $R^{73}$ and $R^{74}$ may be condensed to form a ring; each of $R^{68}$ to $R^{72}$ may form a ring with an adjacent substituent group; $L^7$ denotes a single bond, a substituted or unsubstituted arylene group, or a substituted or unsubstituted heteroarylene group; each of $X^1$ to $X^5$ denotes a carbon atom or a nitrogen atom and when it is a nitrogen atom, the nitrogen atom does not have any of the substituent groups $R^{68}$ to $R^{72}$; $X^1$ to $X^5$ can contain 1 to 4 nitrogen atoms; the derivative is connected to either $L^1$ or $L^2$ in general formula (1-1) given above or either $L^3$ or $L^4$ in general formula (1-2) given above at the position of $R^{67}$; and $C^1$ denotes a carbon atom.

3. A benzindolocarbazole derivative as described in claim 2 that is connected to a group as represented by any of general formulae (2) to (7) at the position of either $L^1$ in general formula (1-1) given above or $L^3$ in general formula (1-2) given above.

4. A benzindolocarbazole derivative as described in claim 3, wherein at least either $A^1$ or $A^2$ in general formula (1-1) given above or at least either $A^3$ or $A^4$ in general formula (1-2) given above is a group as represented by general formula (7) given above and $X^1$, $X^2$, and $X^4$ in general formula (7) given above are nitrogen atoms.

5. A light emitting device material comprising a benzindolocarbazole derivative as described in claim 3.

6. A light emitting device as described in claim 5, wherein at least one of the organic layers is a hole transport layer, the hole transport layer containing the benzindolocarbazole derivative.

7. A light emitting device comprising an anode, a cathode, and organic layers interposed therebetween and emits light by converting electric energy, any of the layers interposed between the anode and the cathode comprising a benzindolocarbazole derivative as described in claim 3.

8. A benzindolocarbazole derivative as described in claim 2, wherein at least either $A^1$ or $A^2$ in general formula (1-1) given above or at least either $A^3$ or $A^4$ in general formula (1-2) given above is a group as represented by general formula (7) given above and $X^1$, $X^2$, and $X^4$ in general formula (7) given above are nitrogen atoms.

9. A light emitting device material comprising a benzindolocarbazole derivative as described in claim 8.

10. A light emitting device as described in claim 9, wherein at least one of the organic layers is a hole transport layer, the hole transport layer containing the benzindolocarbazole derivative.

11. A light emitting device comprising an anode, a cathode, and organic layers interposed therebetween and emits light by converting electric energy, any of the layers interposed between the anode and the cathode comprising a benzindolocarbazole derivative as described in claim 8.

12. A light emitting device material comprising a benzindolocarbazole derivative as described in claim 2.

13. A light emitting device as described in claim 12, wherein at least one of the organic layers is a hole transport layer, the hole transport layer containing the benzindolocarbazole derivative.

14. A light emitting device as described in claim 12, wherein at least one of the organic layers is a hole injection layer, the hole injection layer containing the benzindolocarbazole derivative.

15. A light emitting device comprising an anode, a cathode, and organic layers interposed therebetween and emits light by converting electric energy, any of the layers interposed between the anode and the cathode comprising a benzindolocarbazole derivative as described in claim 2.

16. A light emitting device material comprising a benzindolocarbazole derivative as described in claim 1.

17. A light emitting device as described in claim 16, wherein at least one of the organic layers is a hole transport layer, the hole transport layer containing said benzindolocarbazole derivative.

18. A light emitting device as described in claim 16, wherein at least one of the organic layers is a hole injection layer, the hole injection layer containing said benzindolocarbazole derivative.

19. A light emitting device as described in claim 16, wherein at least one of the organic layers is a light emitting layer, the light emitting layer containing a host material and a dopant material, and the host material being said benzindolocarbazole derivative.

20. A light emitting device comprising an anode, a cathode, and organic layers interposed therebetween and emits light by converting electric energy, any of the layers interposed between the anode and the cathode comprising a benzindolocarbazole derivative as described in claim 1.

* * * * *